(12) United States Patent
Hart et al.

(10) Patent No.: US 8,895,698 B2
(45) Date of Patent: Nov. 25, 2014

(54) BINDING PARTNERS OF ANTIBODIES SPECIFIC FOR DENDRITIC CELL ANTIGENS

(75) Inventors: Derek Nigel Hart, Dutton Park (AU); David Munster, Holland Park (AU); Peter Vukovic, McGregor (AU)

(73) Assignee: The Corporation of the Trustees of the Order of the Sisters of Mercy in Queensland, South Brisbane (AU)

( * ) Notice: Subject to any disclaimer, the term of this patent is extended or adjusted under 35 U.S.C. 154(b) by 116 days.

(21) Appl. No.: 13/606,665

(22) Filed: Sep. 7, 2012

(65) Prior Publication Data

US 2013/0085261 A1    Apr. 4, 2013

Related U.S. Application Data

(62) Division of application No. 11/721,425, filed as application No. PCT/AU2005/001864 on Dec. 9, 2005, now abandoned.

(30) Foreign Application Priority Data

Dec. 10, 2004 (AU) ................................ 2004907069

(51) Int. Cl.
| | |
|---|---|
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| C07K 16/28 | (2006.01) |
| C07K 7/08 | (2006.01) |
| G01N 33/564 | (2006.01) |
| C07K 7/06 | (2006.01) |
| A61K 38/00 | (2006.01) |

(52) U.S. Cl.
CPC ............ C07K 7/08 (2013.01); *C07K 2317/34* (2013.01); C07K 16/28 (2013.01); G01N 33/564 (2013.01); C07K 7/06 (2013.01); *A61K 38/00* (2013.01)
USPC ........................................ 530/327

(58) Field of Classification Search
None
See application file for complete search history.

(56) References Cited

U.S. PATENT DOCUMENTS

| | | | |
|---|---|---|---|
| 5,876,917 | A | 3/1999 | Hart |
| 6,017,719 | A | 1/2000 | Tseng-Law et al. |
| 2003/0109690 | A1 * | 6/2003 | Ruben et al. ................. 536/23.1 |
| 2003/0166277 | A1 | 9/2003 | Zauderer et al. |
| 2004/0005664 | A1 | 1/2004 | Meyers et al. |

FOREIGN PATENT DOCUMENTS

| | | |
|---|---|---|
| WO | 93/09234 A2 | 5/1993 |
| WO | 03/093306 A2 | 11/2003 |

OTHER PUBLICATIONS

Collin, M. et al. 2005 "In Vitro Depletion of Tissue-Derived Dendritic Cells by CMRF-44 Antibody and Alemtuzumab: Implications for the Control of Graft-Versus-Host Disease" Transplantation, 79:722-725.
Dong, R. et al., 1995 "Characterization of T cell epitopes restricted by HLA-DP9 in streptococcal M12 protein" The Journal of Immunology 154:4536-4545.
Koppi, T. et al., 2003 "CMRF-44 antibody-mediated depletion of activated human dendridic cells: a potential means for improving allograft survival" Transplantation 75:1723-1730.
Sigmundsdottir, H. et al., 1997 "Circulating T Cells of Patients with Active Psoriasis Respond to Streptococcal M-Peptides Sharing Sequences with Human Epidermal Keratins" Scandinavian Journal of Immunology 45:688-697.
Progress in Autoimmune Disease, 2005, pp. 1-126.
Gavilondo et al., 2000, "Antibody Engineering at the Millennium" Biotechniques, vol. 29: 128-149.

\* cited by examiner

*Primary Examiner* — Amy Juedes
(74) *Attorney, Agent, or Firm* — Knobbe, Martens, Olson & Bear, LLP

(57) ABSTRACT

The present invention relates to the field of diagnostics, therapeutics and immunological reagents. More particularly, the present invention provides binding partners of antibodies specific for dendritic cell (DC) antigens. The present invention further provides diagnostic and/or therapeutic agent based on the binding partners or antibodies specific for the binding partners.

6 Claims, 23 Drawing Sheets

BINDING PARTNERS OF ANTIBODIES SPECIFIC FOR DENDRITIC CELL ANTIGENS

CROSS REFERENCE TO RELATED APPLICATIONS

This application is a divisional application of U.S. patent application Ser. No. 11/721,425, filed Jan. 8, 2009, which is U.S. National Phase of International Application PCT/AU2005/001864, filed Dec. 9, 2005 designating the U.S. and published in English as WO 2006/060871 on Jun. 15, 2006, which claims priority to Australian Patent Application No. 2004907069 filed Dec. 10, 2004.

BACKGROUND OF THE INVENTION

1. Field of the Invention

The present invention relates generally to the field of diagnostics, therapeutics and immunological reagents. More particularly, the present invention provides binding partners of antibodies specific for dendritic cell (DC) antigens. The present invention further provides diagnostic and/or therapeutic agents based on the binding partners or antibodies specific for the binding partners.

2. Description of the Prior Art

Reference to any prior art in this specification is not, and should not be taken as, an acknowledgment or any form of suggestion that this prior art forms part of the common general knowledge in any country.

Bibliographic details of references provided in this document are listed at the end of the specification.

Dendritic cells (DC) are potent cellular activators of primary immune responses (Hart, *Blood* 90:3245-3287, 1997). Immature myeloid DC in non-lymphoid organs react to, endocytose and process antigens and migrate via blood and lymph to T cell areas of lymphoid organs. Here, the mature cells present foreign peptide complexed to MHC Class II to T cells and deliver unique signals for T-cell activation (immuno-stimulation). They also stimulate B lymphocytes and NK cells. DC undergo differentiation/activation during this process, lose their antigen-capturing capacity and become mature, immuno-stimulatory DC that trigger naïve T-cells recirculating through the lymphoid organs. The lymphoid DC subset may have a different migration pathway and although capable of stimulating allogeneic and autologous T-lymphocytes they have been suggested to have a regulatory function (Grouard et al, *J Exp Med* 185:1101-1111, 1997). As part of the differentiation/activation process, DCs up-regulate certain relatively selectively-expressed cell surface antigens such as the CMRF44 (CMRF44Ag) and CD83 antigens. DC in the thymus and DCs that do not have an activated co-stimulating phenotype probably contribute to central and peripheral tolerance.

Allogeneic transplantation involves the transfer of material from a host to a recipient. In this process, many foreign antigens are introduced into a host and an immune response results when these foreign antigens are detected by the host's immune system. Initially, an immune response involves interactions between the antigen and antigen-presenting cells (APC) such as dendritic cells. Interstitial donor DC in heart and kidney contribute to (direct) recipient T lymphocyte sensitization to all antigens but recipient DC, after migrating into the donor tissue, can also stimulate (indirect) alloantigen sensitization of recipient T-lymphocytes. Depletion of heart and kidney and pancreatic islet DC appears to prolong allograft survival. Interestingly, during liver transplantation, donor leucocytes, which may include non-activated dendritic cells, appear to generate allogeneic tolerance. DC are also predicted to contribute to both acute and chronic Graft Versus Host Disease (GVHD), the major life threatening complication of allogeneic bone marrow transplantation (BMT). Blood DC counts change during acute GVHD and recent data have suggested that the DC subset constitution of the allogeneic stem cell preparation might relate to GVHD outcome. Recent evidence from a mouse model suggests that host APC contribute to the acute GVHD. DC may in certain circumstance prevent acute GVHD.

Monoclonal antibodies which act at the level of the responder T lymphocyte have been investigated as therapeutic immunosuppression agents in allogeneic transplantation. The CD3 reagent OKT3 (Orthoclone, Cilag) is used routinely to treat acute renal allograft rejection. Campath 1 (CD52) and its variants have been used in solid organ transplant and BMT. More recent attempts to suppress acute GVHD have involved the antibody ABX-CBL (CD147) (Deeg et al, *Blood* 98:2052-2058, 2001) and anti-IL-2R mAb Daclizumab (Calm et al, *Transplantation* 60:939-942, 1995). Attempts to interfere with the interaction of the responder T-lymphocyte and an APC have focused on antibodies directed against the co-stimulator molecules CD40, CD80 and CD86 or their ligands. Animal studies suggest that blockade of co-stimulator molecules on DC and other APC induces T cell anergy and prolongation of solid organ grafts (Koenen and Joosten, *Blood* 95:3153-3161, 2000, Kirk et al, *Nat Med* 5:686-693, 1999; Kirk et al, *Proc Natl Acad Sci USA* 94:8789-8794, 1997). The use of CD80, CD86 and CD28 blocking agents prevents acute GVHD in mice (Blazar et al, *Blood* 85:2607-2618, 1995) and in vitro blockage of allogeneic responses in allogeneic stem cell preparations has been used in clinical BMT with initial encouraging results (Gribben et al, *Blood* 87:4887-4893, 1996). The use of a reagent that was more selective at targeting differentiated/activated DC might be advantageous.

In humans, at least two populations of DC, the immature myeloid DC and the plasmacytoid DCs, have been identified based on differential expression of CD11c (O'Doherty et al, *J Exp Med* 178:1067, 1993; O'Doherty et al, *Immunol* 82:487, 1994) More recent studies have shown that CD11c$^-$ DC have a different phenotype and express higher amounts of CD123, and have a morphology and function distinct from CD11c$^+$ DC (Grouard et al, *J Exp Med.* 185:1101-1111, 1997). These two subsets are denoted as myeloid lineage CD11c$^+$ DC and plasmacytoid CD123$^+$ DC. It is thought unlikely that there is a direct developmental relationship between them (Robinson et al, *Eur J Immunol* 29:2769-2778, 1999).

Theoretically, monoclonal antibodies directed at DC administered to the recipient of a solid organ graft would deplete donor DC (i.e. direct) as well as recipient DC (indirect) as they enter the circulation and initiate antigen presentation pathways. Other donor leucocytes may have immunomodulatory capacity. DC depletion therapy might then be ceased after a short period, allowing tolerance to emerge. Depleting recipient DC may be more efficacious than disrupting co-stimulator pathways. Investigation of this concept has been delayed, however, by the absence of suitable DC reagents. CMRF44 antibody (CMRF44Ab) is an antibody specific for DC and is used for the identification and isolation of human blood DC (Hock et al, *Immunology* 83:573-581, 1994; Fearnley et al, *Blood* 89:3708-3716, 1997). The latter authors have shown that the epitope for CMRF44 (i.e. CMRF44Ab) is expressed early in the differentiation of DC from circulating precursor cells. However, the nature of the antigen which is recognized by CMRF44Ab and its role in the regulating DC function has yet to be elucidated.

There is a need, therefore, to be able to identify DC epitopes which are recognized by CMRF44Ab and use these for the rational design of diagnostic and/or therapeutic agents useful for diagnosing, preventing and/or treating immunological diseases and conditions.

SUMMARY OF THE INVENTION

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

Nucleotide and amino acid sequences are referred to by sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided at the end of the specification.

Abbreviations used herein are defined in Table 2.

The present invention relates to binding partners of DC-specific antigens, and in particular, antigens defined by the specificity of CMRF44Ab, and antibodies specific for the binding partners. The present invention further provides diagnostic and/or therapeutic agents based on the binding partners and antibodies which are useful for diagnosing and/or preventing and/or treating immunological diseases and conditions.

In one embodiment, therefore, the present invention provides an isolated binding partner of an antibody which is specific for a DC antigen wherein the antibody comprises the binding specificity of CMRF44Ab. In a particularly preferred embodiment, the present invention provides an isolated binding partner of CMRF44Ab.

The isolated binding partner may be a proteinaceous molecule such as a peptide, polypeptide or protein or a mutant, part, derivative, homolog, analog or mimetic thereof or a non-proteinaceous nucleic acid encoding or mimetic of the peptide, polypeptide or protein such as, but not limited to, small to large natural or synthetically derived organic and inorganic molecules.

In a particularly preferred embodiment of the present invention, the binding partner is a peptide capable of binding to CMRF44Ab.

According to this embodiment, therefore, the present invention provides an isolated peptide comprising the amino acid sequence:

AX₁KX₂Q (SEQ ID NO: 1)

wherein X₁ is any amino acid residue but is preferably L, P or Q and X₂ is any amino acid residue but is preferably E, Y or Q which is capable of binding to CMRF44Ab. Preferred peptides are selected from the listing comprising: AQKYQ (SEQ ID NO:2), APKQQ (SEQ ID NO:3), ALKYQ (SEQ ID NO:4) or ALKEQ (SEQ ID NO:5) In a particularly preferred embodiment, the isolated peptide comprises the sequence:

AQKYQ (SEQ ID NO: 2)

Other peptides covered by the present invention include peptides comprising the amino acid sequence selected from the list comprising:

ALKYQTGMPQSM (SEQ ID NO: 6)

ALKEQGWPGQPL (SEQ ID NO: 7)

ALKYQTGMPQSM (SEQ ID NO: 8)

APKQQYPWWYSS (SEQ ID NO: 9)

AQKYQGIHIWPR (SEQ ID NO: 10)

A particularly useful peptide in the practice of the present invention incorporates the sequence set forth in SEQ ID NO:2, such as but not limited to, the peptide set forth in SEQ ID NO:10.

The binding partners of the present invention are useful for as an antigen for generating immunointeractive molecules, such as antibodies, specific for the binding partner. In a preferred embodiment of the present invention the antibodies are deimmunized, and in particular, dehumanised antibodies.

The binding partners and immunointeractive molecules of the present invention facilitate, inter alia, the development of methods for diagnosing or preventing and/or treating of a range of immunological diseases and conditions in a subject and pharmaceutical compositions useful for same.

As such, the present invention also contemplates the use of a isolated binding partner or immunointeractive molecule of the present invention in the manufacture of a medicament or diagnostic for the diagnosis, treatment and/or prevention of immunological disease, condition, pathology or state of health.

TABLE 1

SUMMARY OF SEQUENCE IDENTIFIERS

| SEQUENCE ID NO: | DESCRIPTION |
|---|---|
| 1 | AX₁KX₂Q |
| 2 | AQKYQ |
| 3 | APKQQ |
| 4 | ALKYQ |
| 5 | ALKEQ |
| 6 | ALKYQTGMPQSM |
| 7 | ALKEQGWPGQPL |
| 8 | ALKYQTGMPQSM |
| 9 | APKQQYPWWYSS |
| 10 | AQKYQGIHIWPR |
| 11 | YHTLQAPTPPGW |
| 12 | VPYIYVNEPLSR |

TABLE 2

ABBREVIATIONS

| ABBREVIATION | DESCRIPTION |
| --- | --- |
| DC | Dendritic cell |
| CMRF44Ab | CMRF44 antibody |
| CMRF44Ag | CMRF44 antigen |

DETAILED DESCRIPTION OF THE INVENTION

Figure 1:
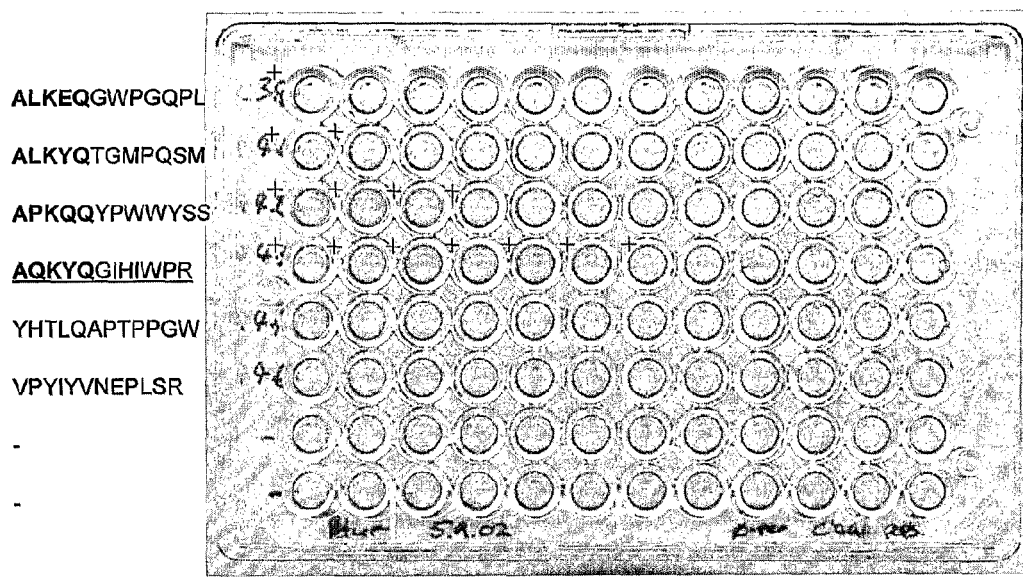
FIG. 1 is a photographic representation of ELISA analysis of a family of binding peptide bacteriophage clones. ALKEQGWPGQPL (SEQ ID NO: 7); ALKYQTGMPQSM (SEQ ID NO: 8); APKQQYPWWYSS (SEQ ID NO: 9); AQKYQGIHIWPR (SEQ ID NO: 10); YHTLQAPTPPGW (SEQ ID NO: 11); and VPYIYVNEPLSR (SEQ ID NO: 12). Wells showings a positive result are indicated by a "+". Color reproductions of all figures are available from the inventor upon request.

Prior to describing the present invention in detail, it is to be understood that unless otherwise indicated, the subject invention is not limited to specific formulation components, manufacturing methods, dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to an "antigen" includes a single antigen, as well as two or more antigens; reference to an "binding partner" includes a single binding partner, as well as two or more binding partners; reference to an "peptide" includes a single peptide, as well as two or more peptides; and so forth.

The present invention relates to binding partners of DC-specific antigens, and in particular, antigens defined by the specificity of CMRF44Ab. In one embodiment, the binding partners are regarded as mimetics of the antigens to which CMRF44Ab interact. These antigens are referred to herein as CMRF44Ag. The term "mimetic" in the context of this invention applies to the functional equivalents of the ability of the mimetics to bind to CMRFAg rather then to structural equivalence or any similarity in biological function as such.

In one embodiment, therefore, the present invention provides an isolated binding partner of an antibody which is specific for a DC antigen wherein the antibody comprises the binding specificity of CMRF44Ab.

In a particularly preferred embodiment, the present invention provides an isolated binding partner of CMRF44Ab.

In the context of the present invention, a "binding partner" may be a proteinaceous molecule such as a peptide, polypeptide or protein or a mutant, part, derivative, homolog, analog or mimetic thereof. In relation to proteinaceous molecules, including peptides, polypeptide and proteins, without distinction, the terms mutant, part, derivative, homolog, analog or mimetic are meant to encompass alternative forms of the binding partner which is capable of binding to CMRF44Ab. Reference herein to peptide, polypeptide or protein also includes fusion molecules such as a peptide, polypeptide or protein fused at or near its amino (N)- or carboxy (C)-terminal to another peptide, polypeptide or protein or having a lipid moiety attached to the amino acid backbone or a side chain of an amino acid residue within the backbone. The binding partner may also be a non-proteinaceous mimetic of the peptide, polypeptide or protein such as, but not limited to, small to large natural or synthetically derived organic and inorganic molecules.

In one preferred embodiment, the binding partner is a peptide capable of binding to CMRF44Ab.

According to this embodiment, therefore, the present invention provides an isolated peptide comprising the amino acid sequence:

$$AX_1KX_2Q \quad \text{(SEQ ID NO: 1)}$$

wherein $X_1$ is any amino acid residue but is preferably L, P or Q and $X_2$ is any amino acid residue but is preferably E, Y or Q which is capable of binding to CMRF44Ab.

The peptide of this aspect of the present invention may comprise the amino acid sequence set forth in SEQ ID NO:1 or it may be part of a larger sequence.

Examples of particular peptides contemplated in respect of this aspect of the present invention include, but are not limited to:

$$AQKYQ \quad \text{(SEQ ID NO: 2)}$$

$$APKQQ \quad \text{(SEQ ID NO: 3)}$$

$$ALKYQ \quad \text{(SEQ ID NO: 4)}$$

$$ALKEQ \quad \text{(SEQ ID NO: 5)}$$

The most preferred peptide in respect of this aspect of the present invention is:

$$AQKYQ \quad \text{(SEQ ID NO: 2)}$$

Accordingly, another aspect of the present invention is directed to an isolated peptide comprising an amino acid sequence selected from AQKYQ (SEQ ID NO:2), APKQQ (SEQ ID NO:3), ALKYQ (SEQ ID NO:4) or ALKEQ (SEQ ID NO:5) which is capable of binding to CMRF44Ab.

In another embodiment, the present invention provides an isolated peptide comprising the amino acid sequence selected from the list comprising:

$$ALKYQTGMPQSM \quad \text{(SEQ ID NO: 6)}$$

$$ALKEQGWPGQPL \quad \text{(SEQ ID NO: 7)}$$

$$ALKYQTGMPQSM \quad \text{(SEQ ID NO: 8)}$$

$$APKQQYPWWYSS \quad \text{(SEQ ID NO: 9)}$$

$$AQKYQGIHIWPR \quad \text{(SEQ ID NO: 10)}$$

which are capable of binding to CMRF44Ab.

As described hereinbefore, reference herein to a proteinaceous molecule such as a peptide, polypeptide or protein also includes a mutant, section, derivative, homolog, analog or mimetic thereof.

Mutant forms of the peptides may be naturally occurring or artificially generated variants of the binding partner which are capable of binding to CMRF44Ab comprising one or more amino acid substitutions, deletions or additions. Mutants may be induced by mutagenesis or other chemical methods or generated recombinantly or synthetically. Alanine scanning is a useful technique for identifying important amino acids (Wells, *Methods Enzymol* 202:2699-2705, 1991). In this technique, an amino acid residue is replaced by Alanine and its effect on the peptide's activity is determined. Each of the amino acid residues of the peptide is analyzed in this manner to determine the important regions of the polypeptide. Mutants are tested for their ability to bind to CMRF44Ab and for other qualities such as, but not limited to, longevity.

Sections of the binding partners of the present invention may encompass CMRF44Ab binding portions of the full-length binding partner which is capable of binding to CMRF44Ab. Sections are at least 3, preferably at least 4 and more preferably at least 5 contiguous amino acids, which exhibit the requisite activity. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of an amino acid sequence of the invention with proteinases such as endoLys-C, endoArg-C, endoGlu-C and *staphylococcus* V8-protease. The digested fragments can be purified by, for example, high performance liquid chromatographic (HPLC) techniques.

Thus, binding partners encompass mutants, sections, derivatives, homologs, analogs as well as hybrid or fusion molecules and glycosylaton variants. Derivatives also include molecules having a percent amino acid sequence identity over a window of comparison after optimal alignment. Preferably, the percentage similarity between a particular derivative and an amino acid sequence described herein is at least about 80% such as at least about 80, 81, 82, 83, 84, 85, 86, 87, 88, 89, 90, 91, 92, 93, 94, 95, 96, 97, 98, 99 and 100%.

Analogs of the binding partners contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogs. This term also does not exclude modifications of the polypeptide, for example, glycosylations, acetylations, phosphorylations and the like. Included within the definition are, for example, polypeptides containing one or more analogs of an amino acid (including, for example, unnatural amino acids such as those given in Table 3) or polypeptides with substituted linkages. Such polypeptides may need to be able to enter the cell and/or cross the blood-brain barrier.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids, contemplated herein is shown in Table 3.

TABLE 3

CODES FOR NON-CONVENTIONAL AMINO ACIDS

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |

TABLE 3-continued

CODES FOR NON-CONVENTIONAL AMINO ACIDS

| Non-conventional amino acid | Code | Non-conventional amino acid | Code |
|---|---|---|---|
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenyl-ethylamino)cyclopropane | Nmbc | | |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogs by introducing covalent bonds such as forming an amide bond between the N and C termini, between two side chains or between a side chain and the N or C terminus.

In relation to the present invention, mimetics are another useful group of molecules. The term is intended to refer to a substance which has some chemical similarity to the molecule it mimics, such as, for example, CMRF44Ag, but which antagonizes or agonizes (mimics) its interaction with a target, such as, for example, CMRF44Ab. A peptide mimetic may be a peptide-containing molecule that mimics elements of protein secondary structure (Johnson et al., *Peptide Turn Mimetics in Biotechnology and Pharmacy*, Pezzuto et al., Eds., Chapman and Hall, New York, 1993). The underlying rationale behind the use of peptide mimetics is that the peptide backbone of proteins exists chiefly to orient amino acid side chains in such a way as to facilitate molecular interactions such as those of antibody and antigen, enzyme and substrate or scaffolding proteins. A peptide mimetic, therefore, is designed to permit molecular interactions similar to the natural molecule.

The designing of mimetics to a pharmaceutically active compound is a known approach to the development of pharmaceuticals based on a "lead" compound. This might be desirable where the active compound is difficult or expensive to synthesize or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g. by substituting each residue in turn. As described hereinbefore, Alanine scans of peptides are commonly used to refine such peptide motifs. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, x-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of a receptor and ligand are modelled. This can be especially useful where the receptor and/or ligand change conformation on binding, allowing the model to take account of this in the design of the mimetic. Modelling can be used to generate agents which interact with the linear sequence or a three-dimensional configuration.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

The goal of rational drug design is to produce structural analogs of biologically active polypeptides of interest or of small molecules with which they interact (e.g. agonists, antagonists, inhibitors or enhancers) in order to fashion drugs which are, for example, more active or stable forms of the polypeptide, or which, for example, enhance the function of a polypeptide in vivo (see, e.g. Hodgson, *Bio/Technology* 9:19-21, 1991). In one approach, one first determines the three-dimensional structure of a protein of interest by x-ray crystallography, by computer modelling or most typically, by a combination of approaches. Useful information regarding the structure of a polypeptide may also be gained by modelling based on the structure of homologous proteins. An example of rational drug design is the development of HIV protease inhibitors (Erickson et al, *Science* 249:527-533, 1990).

The present invention also extends to genetic molecules, such as nucleic acid sequences, which encode the proteinaceous molecules described herein.

A target nucleic acid sequence or a part of a nucleic acid sequence, such as the nucleic acid sequence encoding SEQ ID NOs: 1 to 10, may be introduced into a cell in a vector such that the nucleic acid sequence remains extrachromosomal. In such a situation, the nucleic acid sequence will be expressed by the cell from the extrachromosomal location. Vectors for introduction of nucleic acid sequence both for recombination and for extrachromosomal maintenance are known in the art and any suitable vector may be used. Methods for introducing nucleic acids into cells such as electroporation, calcium phosphate co-precipitation and viral transduction are known in the art.

In particular, a number of viruses have been used as nucleic acid transfer vectors or as the basis for preparing nucleic acid transfer vectors, including papovaviruses (e.g. SV40, Madzak et al, *J Gen Virol* 73:1533-1536, 1992), adenovirus (Berkner, *Curr Top Microbiol Immunol* 158:39-66, 1992; Berkner et al, *BioTechniques* 6:616-629, 1988; Gorziglia and Kapikian, *J Virol* 66:4407-4412, 1992; Quantin et al, *Proc Natl Acad Sci USA* 89:2581-2584, 1992; Rosenfeld et al, *Cell* 68:143-155, 1992; Wilkinson et al, *Nucleic Acids Res* 20:233-2239, 1992; Stratford-Perricaudet et al, *Hum Gene Ther* 1:241-256, 1990; Schneider et al, *Nat Genetics* 18:180-183, 1998), vaccinia virus (Moss, *Curr Top Microbiol Immunol* 158: 5-38, 1992; Moss, *Proc Natl Acad Sci USA* 93:11341-11348, 1996), adeno-associated virus (Muzyczka, *Curr Top Microbiol Immunol* 158:97-129, 1992; Ohi et al, *Gene* 89:279-282, 1990; Russell and Hirata, *Nat Genetics* 18:323-328, 1998), herpesviruses including HSV and EBV (Margolskee, *Curr Top Microbiol Immunol* 158:67-95, 1992; Johnson et al, *J Virol* 66:2952-2965, 1992; Fink et al, *Hum Gene Ther* 3:1-19, 1992; Breakefield and Geller, *Mol Neurobiol* 1:339-371, 1987; Freese et al, *Biochem Pharmaco.* 40:2189-2199, 1990; Fink et al, *Ann Rev Neurosci* 19:265-287, 1996), lentiviruses (Naldini et al, *Science* 272:263-267, 1996), Sindbis and Semliki Forest virus (Berglund et al, *Biotechnology* 11:916-920, 1993) and retroviruses of avian (Bandyopadhyay and Temin, *Mol Cell Biol* 4:749-754, 1984; Petropoulos et al, *J Virol* 66:3391-3397, 1992), murine (Miller, *Curr Top Microbiol Immunol* 158:1-24, 1992; Miller et al, *Mol Cell Biol* 5:431-437, 1985; Sorge et al, *Mol Cell Biol* 4:1730-1737, 1984; Mann and Baltimore, *J Virol* 54:401-407, 1985; Miller et al, *J Virol* 62:4337-4345, 1988) and human (Shimada et al, *J Clin Invest* 88:1043-1047, 1991; Helseth et al, *J Virol* 64:2416-2420, 1990; Page et al, *J Virol* 64:5270-5276, 1990; Buchschacher and Panganiban, *J Virol* 66:2731-2739, 1982) origin.

Non-viral nucleic acid transfer methods are known in the art such as chemical techniques including calcium phosphate co-precipitation, mechanical techniques, for example, microinjection, membrane fusion-mediated transfer via liposomes and direct DNA uptake and receptor-mediated DNA transfer. Viral-mediated nucleic acid transfer can be combined with direct in vivo nucleic acid transfer using liposome delivery, allowing one to direct the viral vectors to particular cells. Alternatively, the retroviral vector producer cell line can be injected into particular tissue. Injection of producer cells would then provide a continuous source of vector particles.

In relation to the genetic molecules of the present invention, the terms mutant, section, derivative, homolog, analog or mimetic have analogous meanings to the meanings ascribed to these forms in relation to proteinaceous molecules. In all cases, variant forms are tested for their ability to function as proposed herein using techniques which are set forth herein or which are selected from techniques which are currently well known in the art.

When in nucleic acid form, a derivative comprises a sequence of nucleotides having at least 60% identity to a parent molecule, such as a nucleic acid sequence encoding a binding partner of the present invention, or a section thereof. A "section" of a nucleic acid molecule is defined as having a minimal size of at least about 9 nucleotides or preferably about 12 nucleotides or more preferably at least about 15 nucleotides. This definition includes all sizes in the range of 9-15 nucleotides including 9, 10, 11, 12, 13, 14 or 15, nucleotides as well as greater than 15 nucleotides including 50, 100, 300, 500, 1000 nucleotides or nucleic acid molecules having any number of nucleotides within these values. Having at least about 60% identity means, having optimal alignment, a nucleic acid molecule comprises at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% identity with a reference sequence which encodes a binding partner of the present invention.

The terms "similarity" or "identity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and amino acid sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al (*Nucl Acids Res* 25:3389-3402, 1997). A detailed discussion of sequence analysis can be found in Unit 19.3 of Ausubel et al ("Current Protocols in Molecular Biology" John Wiley & Sons Inc, 1994-1998, Chapter 15).

The terms "sequence similarity" and "sequence identity" as used herein refer to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e. the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

The terms "nucleic acids", "nucleotide" and "polynucleotide" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog (such as the morpholine ring), internucleotide modifications such as uncharged linkages (e.g. methyl phosphonates, phosphotriesters, phosphoamidates, carbamates, etc.), charged linkages (e.g. phosphorothioates, phosphorodithioates, etc.), pendent moieties (e.g. polypeptides), intercalators (e.g. acridine, psoralen, etc.), chelators, alkylators and modified linkages (e.g. $\alpha$-anomeric nucleic acids, etc.). Also included are synthetic molecules that mimic polynucleotides in their ability to bind to a designated sequence via hydrogen binding and other chemical interactions. Such molecules are known in the art and include, for example, those in which peptide linkages substitute for phosphate linkages in the backbone of the molecule.

The genetic molecules of the present invention are also capable of hybridizing to other genetic molecules. Reference herein to "hybridizes" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low).

Reference herein to a "low stringency" includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as "medium stringency", which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or "high stringency", which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty, *J Mol Biol* 5:109-118, 1962). However, the $T_m$ of a duplex nucleic acid molecule decreases by 1° C. with every increase of 1% in the number of mismatch base pairs (Bonner and Laskey, *Eur J Biochem* 46:83-88, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The capability of the binding partners of the present invention, whether they be proteinaceous or non-proteinaceous, to interact with CMRF44Ab may be assessed via a number of screening methods which would be well known to a person skilled in the art. These may include screening naturally produced libraries, chemical produced libraries, as well as combinatorial libraries, phage display libraries and in vitro translation-based libraries. One method of screening utilizes eukaryotic or prokaryotic host cells which are stably transformed with recombinant polynucleotides expressing a target peptide of interest, preferably in competitive binding assays. Such cells, either in viable or fixed form, can be used for standard binding assays. One may measure, for example, the formation of complexes between CMRF44Ab and the binding partner being tested.

The screening procedure includes assaying (i) for the presence of a complex between the drug and the target. As described hereinbefore, one form of assay involves competitive binding assays. In such competitive binding assays, the target, such as CMRF44Ab, is typically labeled. Free target is separated from any putative complex and the amount of free (i.e. uncomplexed) label is a measure of the binding of the binding partner being tested to target molecule. One may also measure the amount of bound, rather than free, target. It is also possible to label the binding partner rather than the target and to measure the amount of binding partner binding to target.

Another technique for screening provides high throughput screening for binding partners having suitable binding affinity to a target and is described in detail in Geysen (International Patent Publication No. WO 84/03564). Briefly stated, large numbers of different small peptide test compounds are synthesized on a solid substrate, such as plastic pins or some other surface. The peptide test compounds are reacted with a target and washed. Bound target molecule is then detected by methods well known in the art. This method may be adapted for screening for non-peptide, chemical entities such as small to large natural or synthetically derived organic and inorganic molecules. This aspect, therefore, extends to combinatorial approaches to screening for binding partners.

Purified target can be coated directly onto plates for use in the aforementioned drug screening techniques. However, non-neutralizing antibodies to the target may also be used to immobilize the target on the solid phase. The target may alternatively be expressed as a fusion protein with a tag conveniently chosen to facilitate binding and identification.

The CMRF44Ab binding partners of the present invention, whether in proteinaceous or non-proteinaceous form, are useful in a range of diagnostic and/or therapeutic applications. For example, a binding partner may be used as an antigen to vaccinate an animal in order to generate immunointeractive molecules, such as antibodies, specific for the binding partner. Animals in this regard may include, inter alia, mice, rats, rabbits, cats, dogs, horses, cows, goats, sheep and camels. Such antibodies may be subjected to deimmunization protocols to generate, for example, a humanized DC-specific antibody.

The term "antigen" is used herein in its broadest sense to refer to an agent that is capable of reacting in and/or inducing an immune response. Reference to an "antigen" includes an antigenic determinant or epitope. By "antibody" is meant a protein of the immunoglobulin family that is capable of combining, interacting or otherwise associating with an antigen. An antibody is, therefore, an antigen-binding agent or an "immunointeractive agent". Any agent that has binding affinity for a target antigen is referred to as an immunointeractive agent. It will be understood that this term extends to immunoglobulins (e.g. polyclonal or monoclonal antibodies), immunoglobulin fragments and non-immunoglobulin derived protein frameworks that exhibit antigen-binding activity. The terms "immunointeractive agent" and "antibody" include deimmunized forms of these molecules. An "antibody" is, therefore, an example of an immunointeractive agent and includes a polyclonal or monoclonal antibody. The preferred immunointeractive agents of the present invention are monoclonal antibodies. An antibody includes parts thereof including $F_{ab}$ portions and antigen-binding determinants.

The term "immunoglobulin" is used herein to refer to a protein consisting of one or more polypeptides substantially encoded by immunoglobulin genes. The recognized immunoglobulin genes include the κ, λ, α, γ ($IgG_1$, $IgG_2$, $IgG_3$, $IgG_4$), δ, ε and μ constant region genes, as well as the myriad of other immunoglobulin variable region genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions ($V_L$ and $V_H$ respectively) are together responsible for binding to an antigen, and the constant regions are responsible for the antibody effector functions. In addition to antibodies, immunoglobulins may exist in a variety of other forms including, for example, Fv, scFv, Fab, Fab' and $(Fab')_2$.

That part of an antigen against which a particular immune response is directed is referred to as an "antigenic determinant" or "epitope" and includes a hapten. Typically, in an animal, antigens present several or even many epitopes simultaneously. A "hapten" is a substance that can combine specificity with an antibody but cannot or only poorly induces an immune response unless bound to a carrier. A hapten typically comprises a single antigenic determinant or epitope.

Immunization and subsequent production of monoclonal antibodies may be done using any methods known to those of skill in the art. For examples see: Köhler and Milstein (*Nature* 256:495-499, 1975; Köhler and Milstein, *Eur J Immunol* 6:511-519, 1976), Coligan et al (*Current Protocols in Immunology*, John Wiley & Sons, Inc., 1991-1997) or Toyama et al ("*Monoclonal Antibody, Experiment Manual*", published by Kodansha Scientific, 1987). Essentially, an animal is immunized with an antigen-containing biological fluid or fraction thereof by standard methods to produce antibody-producing cells, particularly antibody-producing somatic cells (e.g. B-lymphocytes, splenocytes). These cells can then be removed from the immunized animal for immortalization. The antigen may need to first be associated with a larger molecule. The latter is any substance of typically high molecular weight to which a non- or poorly immunogenic substance (e.g. a hapten) is naturally or artificially linked to enhance its immunogenicity.

In this aspect of the present invention, the antigen is preferably a DC antigen, such as but not limited to, the CMRF44 antigen.

Immortalization of antibody-producing cells may be carried out using methods, which are well known in the art. For example, the immortalization may be achieved by the transformation method using Epstein-Barr virus (EBV) (Kozbor et al, *Methods in Enzymology* 121:140-167, 1986). In a preferred embodiment, antibody-producing cells are immortalized using the cell fusion method (described in Coligan et al, 1991-1997, supra), which is widely employed for the production of monoclonal antibodies. In this method, somatic antibody-producing cells with the potential to produce antibodies, particularly B cells, are fused with a myeloma cell line. These somatic cells may be derived from the lymph nodes, spleens and peripheral blood of primed animals, preferably rodent animals such as mice and rats. In the exemplary embodiment of this invention mice, spleen cells are used. The use, however, of rat, rabbit, sheep and goat cells, or cells from other animal species is also contemplated.

Specialized myeloma cell lines have been developed from lymphocytic tumors for use in hybridoma-producing fusion procedures (Köhler and Milstein, *Eur J Immunol* 6:511-519, 1976; Shulman et al, *Nature* 276:269-270, 1978; Volk et al, *J Virol* 42:220-227, 1982). These cell lines have been developed for at least three reasons. The first is to facilitate the selection of fused hybridomas from unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocytic tumor cells to produce their own antibodies. To eliminate the production of tumor cell antibodies by the hybridomas, myeloma cell lines incapable of producing endogenous light or heavy immunoglobulin chains are used. A third reason for selection of these cell lines is for their suitability and efficiency for fusion.

Many myeloma cell lines may be used for the production of fused cell hybrids, including, e.g. P3X63-Ag8, P3X63-AG8.653, P3/NS1-Ag4-1 (NS-1), Sp2/0-Ag14 and S194/5.XXO.Bu.1. The P3X63-Ag8 and NS-1 cell lines have been described by Köhler and Milstein (*Eur J Immunol* 6:511-519, 1976). Shulman et al (*Nature* 276:269-270, 1978) developed the Sp2/0-Ag14 myeloma line. The S194/5.XXO.Bu.1 line was reported by Trowbridge (*J Exp Med* 148:313-323, 1978).

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described (Köhler and Milstein, *Nature* 256:495-499, 1975; Köhler and Milstein, *Eur J Immunol* 6:511-519, 1976; Gefter et al, *Somatic Cell Genet* 3:231-236, 1977; Volk et al, *J Virol* 42:220-227, 1982). The fusion-promoting agents used by those investigators were Sendai virus and polyethylene glycol (PEG).

Because fusion procedures produce viable hybrids at very low frequency (e.g. when spleens are used as a source of somatic cells, only one hybrid is obtained for roughly every $1 \times 10^5$ spleen cells), it is preferable to have a means of selecting the fused cell hybrids from the remaining unfused cells, particularly the unfused myeloma cells. A means of detecting the desired antibody-producing hybridomas among other resulting fused cell hybrids is also necessary. Generally, the selection of fused cell hybrids is accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused cell hybrids survive due to the HPRT-positive genotype of the spleen cells. The use of myeloma cells with different genetic deficiencies (drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radioimmunoassay techniques as, for example, described in Kennet et al. ((eds) *Monoclonal Antibodies and Hybridomas: A New Dimension in Biological Analyses*, pp. 376-384, Plenum Press, New York, 1980). In a particularly preferred embodiment, an enzyme linked immunosorbent assay (ELISA) is performed to select the desired anti-idiotypic antibody-producing clones.

Once the desired fused cell hybrids have been selected and cloned into individual antibody-producing cell lines, each cell line may be propagated in either of two standard ways. A suspension of the hybridoma cells can be injected into a histocompatible animal The injected animal will then develop tumors that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

The cell lines are tested for their specificity to detect the antigen of interest by any suitable immunodetection means. For example, cell lines can be aliquoted into a number of wells and incubated and the supernatant from each well is analyzed by enzyme-linked immunosorbent assay (ELISA), indirect fluorescent antibody technique, or the like. The cell line(s) producing a monoclonal antibody capable of recognizing the target idiotype but which does not recognize non-target antigens or epitopes are identified and then directly cultured in vitro or injected into a histocompatible animal to form tumors and to produce, collect and purify the required antibodies.

Non-animal cells such as a plant, yeast and/or microbial cells may also be used to generate, typically, single-chain antibodies. In this embodiment, such cells are engineered to express nucleic acid molecules which encode a chain of an antibody.

As stated hereinbefore, the preferred antibodies of the present invention are deimmunized for use in humans. However, the subject invention also extends to antibodies from any source and deimmunized for use in any host. Examples of animal sources and hosts include, but are not limited to, humans and non-human primates (e.g. guerilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer), reptiles or amphibians (e.g. cane toad), fish (e.g. zebrafish) and other organisms (e.g. *C. elegans*). The deimmunized antibodies or part thereof may also be generated in non-animal sources, such as but not limited to, plants. In this regard, and as noted hereinbefore, plants are particularly useful as a source of "plantibodies" such as single chain antibodies.

Antibodies are deimmunized by being subjected to a deimmunization means. Such a process may take any of a number of forms including the preparation of "chimeric" antibodies which have the same or similar specificity as the monoclonal antibodies prepared according to the present invention. Chimeric antibodies are antibodies whose light and heavy chain genes have been constructed, typically by genetic engineering, from immunoglobulin variable and constant region genes belonging to different species. Thus, in accordance with the present invention, once a hybridoma producing the desired monoclonal antibody is obtained, techniques are used to produce interspecific monoclonal antibodies wherein the binding region of one species is combined with a non-binding region of the antibody of another species (Liu et al, *Proc Natl Acad Sci USA* 84:3439-3443, 1987). For example, the complementary determining regions (CDRs) from a non-human (e.g. murine) monoclonal antibody can be grafted onto a human antibody, thereby "humanizing" the murine antibody (European Patent Publication No. 0 239 400; Jones et al, *Nature* 321:522-525, 1986; Verhoeyen et al, *Science* 239:1534-1536, 1988; Riechmann et al, *Nature* 332:323-327, 1988). In this case, the deimmunizing process is specific for humans. More particularly, the CDRs can be grafted onto a human antibody variable region with or without human constant regions. The non-human antibody providing the CDRs is typically referred to as the "donor" and the human antibody providing the framework is typically referred to as the "acceptor". Constant regions need not be present, but if they are, they must be substantially identical to human immunoglobulin constant regions, i.e. at least about 85-90%, preferably about 95% or more identical. Hence, all parts of a humanized antibody, except possibly the CDRs, are substantially identical to corresponding parts of natural human immunoglobulin sequences. Thus, a "humanized antibody" is an antibody comprising a humanized light chain and a humanized heavy chain immunoglobulin. A donor antibody is said to be "humanized", by the process of "humanization", because the resultant humanized antibody is expected to bind to the same antigen as the donor antibody that provides the CDRs. Reference herein to "humanized" includes reference to an antibody deimmunized to a particular host, in this case, a human host.

Exemplary methods which may be employed to produce deimmunized antibodies according to the present invention are described, for example, in Riechmann et al, *Nature* 332: 323-327, 1988; U.S. Pat. Nos. 6,056,957, 6,180,370 and 6,180,377 and Chothia et al, *J Mol Biol* 196:901-917, 1987.

As used herein, the term "CDR" includes CDR structural loops which covers to the three light chain and the three heavy chain regions in the variable portion of an antibody framework region which bridge β strands on the binding portion of the molecule. These loops have characteristic canonical structures (Chothia et al, *J Mol Biol* 227:799-817, 1992; Rabat et al, "*Sequences of Proteins of Immunological Interest*", U.S. Department of Health and Human Services, 1983).

In the context of the present invention, the term "heavy chain variable region" means a polypeptide which is from about 110 to 125 amino acid residues in length, the amino acid sequence of which corresponds to that of a heavy chain of a monoclonal antibody of the invention, starting from the amino-terminal (N-terminal) amino acid residue of the heavy chain. Likewise, the term "light chain variable region" means a polypeptide which is from about 95 to 130 amino acid residues in length, the amino acid sequence of which corresponds to that of a light chain of a monoclonal antibody of the invention, starting from the N-terminal amino acid residue of the light chain. Full-length immunoglobulin "light chains" (about 25 Kd or 214 amino acids) are encoded by a variable region gene at the $NH_2$-terminus (about 110 amino acids) and a κ or λ constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g. γ (encoding about 330 amino acids).

An immunoglobulin light or heavy chain variable region, which is interrupted by three hypervariable regions, also called CDRs, is referred to herein as a "framework region". The extent of the framework region and CDRs have been precisely defined. The sequences of the framework regions of different light or heavy chains are relatively conserved within a species. As used herein, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDRs. The CDRs are primarily responsible for binding to an epitope of an antigen.

One preferred deimmunization process referred to herein is variable region grafting and results in a "chimeric" antibody. The resulting antibody comprises one or more amino acid substitutions within the v-region when compared to the present (e.g. murine) antibody. The rationale for making v-region changes is to further the potential for an induced immune response in the intended host (e.g. a human). The basis of deimmunization is predicated in part on the assumption that a substantive immune response to an introduced antibody requires a T-cell mediated response. The trigger for the T-cell response is the presentation of processed peptides emanating from the introduced antibody on the surface of antigen presenting cells (APCs). The APCs present such peptides in association with surface MHC class II molecules. The deimmunized approach is, therefore, based on:—
(i) predicting peptide sequences capable of associating with MHC class II molecules; and
(ii) changing strategic residues to eliminate the ability of the peptide to associate with the MHC class II molecule.

The invention also contemplates the generation and use of fragments of monoclonal antibodies produced by the method of the present invention including, for example, Fv, scFv, Fab, Fab' and $F(ab')_2$ fragments. Such fragments may be prepared by standard methods as for example described by Coligan et al (1991-1997, supra).

The present invention also contemplates synthetic or recombinant antigen-binding molecules with the same or similar specificity as the antibodies of the invention. Antigen binding molecules of this type may comprise a synthetic stabilized Fv fragment. Exemplary fragments of this type include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent. ScFvs may be prepared, for example, in accordance with methods outlined in Krebber et al (*J Immunol Methods* 201:35-55, 1997). Alternatively, they may be prepared by methods described in U.S. Pat. No. 5,091,513, European Patent No 239,400 or the articles by Winter and Milstein (*Nature* 349: 293-299, 1991) and Plückthun et al (*In Antibody engineering: A practical approach* 203-252, 1996).

Alternatively, the synthetic stabilised Fv fragment comprises a disulphide stabilized Fv (dsFv) in which cysteine residues are introduced into the $V_H$ and $V_L$ domains such that in the fully folded Fv molecule the two residues will form a disulphide bond therebetween. Suitable methods of producing dsFv are described, for example, in (Glockshuber et al, *Biochem* 29:1363-1367, 1990; Reiter et al, *J Biol Chem* 269:

18327-18331, 1994; Reiter et al, *Biochem* 33:5451-5459, 1994; Reiter et al, *Cancer Res* 54:2714-2718, 1994; Webber et al, *Mol Iminunol* 32:249-258, 1995).

Also contemplated as synthetic or recombinant antigen-binding molecules are single variable region domains (termed dAbs) as, for example, disclosed in (Ward et al, *Nature* 341:544-546, 1989; Hamers-Casterman et al, *Nature* 363:446-448, 1993; Davies and Riechmann, *FEBS Lett* 339:285-290, 1994).

Alternatively, the synthetic or recombinant antigen-binding molecule may comprise a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821.

In an alternate embodiment, the synthetic or recombinant antigen binding molecule may comprise non-immunoglobulin derived, protein frameworks. For example, reference may be made to Ku and Schutz (*Proc Natl Acad Sci USA* 92:6552-6556, 1995) which discloses a four-helix bundle protein cytochrome b562 having two loops randomized to create CDRs, which have been selected for antigen binding.

The synthetic or recombinant antigen-binding molecule may be multivalent (i.e. having more than one antigen binding site). Such multivalent molecules may be specific for one or more antigens. Multivalent molecules of this type may be prepared by dimerization of two antibody fragments through a cysteinyl-containing peptide as, for example disclosed by (Adams et al, *Cancer Res* 53:4026-4034, 1993; Cumber et al, *J Immunol* 149:120-126, 1992). Alternatively, dimerization may be facilitated by fusion of the antibody fragments to amphiphilic helices that naturally dimerize (Plünckthun, *Biochem* 31:1579-1584, 1992) or by use of domains (such as leucine zippers jun and fos) that preferentially heterodimerize (Kostelny et al, *J Immunol* 148:1547-1553, 1992). In further embodiment, a multi-step process is employed such as first administering a deimmunized antibody and then an anti-antibody with, for example, a reporter molecule.

It will be understood that any of the synthetic antibodies described herein may comprise additional modifications such as conservative amino acid substitutions which have substantially no effect on antigen binding or other immunoglobulin functions. Exemplary conservative substitutions may be made according to Table 4.

TABLE 4

EXEMPLARY CONSERVATIVE SUBSTITUTIONS

| ORIGINAL RESIDUE | EXEMPLARY SUBSTITUTIONS |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |

TABLE 4-continued

EXEMPLARY CONSERVATIVE SUBSTITUTIONS

| ORIGINAL RESIDUE | EXEMPLARY SUBSTITUTIONS |
| --- | --- |
| Tyr | Trp, Phe |
| Val | Ile, Leu |

The present invention further encompasses chemical analogs of amino acids in the deimmunized murine monoclonal antibodies described herein. The use of chemical analogs of amino acids is useful inter alia to stabilize the deimmunized murine monoclonal antibodies when administered to a subject. As described hereinbefore, the analogs of the amino acids contemplated herein include, but are not limited to, modifications of side chains, incorporation of unnatural amino acids and/or their derivatives during peptide, polypeptide or protein synthesis and the use of crosslinkers and other methods which impose conformational constraints on the proteinaceous molecule or their analogs.

The binding partners and immunointeractive molecules of the present invention facilitate the development of methods for diagnosing or preventing and/or treating of a range of immunological diseases and conditions in a subject characterized by an unwanted or undesirable immune response. Such conditions include, inter alia, those wherein the response is inappropriate as well as those wherein the response may be regarded as being physiologically normal but is nevertheless undesirable. Examples include, inter alia, autoimmune conditions, chronic inflammatory conditions, asthma and hypersensitivity, allergies to innocuous agents and transplant rejection.

Reference herein to "treatment" may mean a reduction in the severity of an existing disease or condition. The term "treatment" is also taken to encompass "prophylactic treatment" to prevent the onset of a disease or condition. The term "treatment" does not necessarily imply that a subject is treated until total recovery. Similarly, "prophylactic treatment" does not necessarily mean that the subject will not eventually contract a disease or condition.

Subject as used herein refers to humans and non-human primates (e.g. guerilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer), reptiles or amphibians (e.g. cane toad), fish (e.g. zebrafish) and any other organisms (e.g. *C. elegans*) who can benefit from the agents of the present invention. There is no limitation on the type of animal that could benefit from the presently described agents. The most preferred subject of the present invention is a human. A subject regardless of whether it is a human or non-human organism may be referred to as a patient, individual, animal, host or recipient.

In relation to methods of preventing and/or treating the immunological diseases and conditions contemplated herein, the binding partners or immunointeractive molecules of the present invention may be administered directly to a subject or the subjects cells, such as but not limited to DC, may be isolated, contacted in vitro with the binding partners or immunointeractive molecules and then transplanted back to the subject, i.e. DC therapy.

In relation to methods of diagnosing the immunological diseases and conditions contemplated herein, the binding partners, and in particular, the immunointeractive molecules of the present invention, may be used in accordance with any method known to a person skilled in the art which is useful for diagnosing the presence of, or the predisposition to developing, a particular disease or condition. Immunonological-based tests are preferred in this regard and these may include immunohistochemical staining, FACS sorting and the like. A particularly preferred use of the peptide binding partners of the present invention is as a release agent in a non-enzymatic method for the positive selection of target cells, such as DC, from a heterogeneous cell suspension. An example of this method is disclosed in U.S. Pat. No. 6,017,719. The method generally includes forming with a heterogeneous cell suspension a complex comprising a cell separation means such as a paramagnetic bead linked to a primary antibody, which in turn is bound to a cell surface antigen on the target cells. The complex is separated from the cell suspension, and then contacted with a specific peptide which binds to the primary antibody and thereby releases the target cell from the complex.

The present invention also provides pharmaceutical compositions useful for various therapeutic applications in a subject. In this regard, the binding partners or immunointeractive molecules of the present invention can be combined with one or more pharmaceutically acceptable carriers and/or diluents to form the pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g., Remington's Pharmaceutical Sciences, 18$^{th}$ Edition, Mack Publishing Company, Easton, Pa., 1990 ("Remington's").

In relation to immunointeractive molecules, the pharmaceutical compositions of the present invention suitable for use with the diagnostic and/or therapeutic methods described hereinbefore include sterile aqueous solutions as well as lyophilized forms of antibody preparations together with stabilizing agents such as sugar, proteins or other compounds or molecules. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization.

Pharmaceutically acceptable carriers and/or diluents include any and all solvents, dispersion media, coatings, antibacterial and anti-fungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

The pharmaceutical compositions of the invention can be administered in a variety of unit dosage forms depending upon the method of administration. Dosages for typical pharmaceutical compositions are well known to those of skill in the art. Such dosages are typically advisorial in nature and are adjusted depending on the particular therapeutic context, patient tolerance, etc. The amount of agent adequate to accomplish this is defined as the "effective amount". The dosage schedule and effective amounts for this use, i.e., the "dosing regimen" will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., Remington's; Egleton and Davis, *Peptides* 18:1431-1439, 1997; Langer, *Science* 249:1527-1533, 1990.

The pharmaceutical compositions defined in accordance with the present invention may also be co-administered with one or more other pharmaceutical compositions. Reference herein to "co-administered" means simultaneous administration in the same formulation or in two different formulations via the same or different routes or sequential administration by the same or different routes. Reference herein to "sequential" administration is meant a time difference of from seconds, minutes, hours or days between the administration of the two types of agents and/or pharmaceutical compositions. Co-administration of the agents and/or pharmaceutical compositions may occur in any order.

The present invention is further described by the following non-limiting examples.

EXAMPLE 1

Isolation of Peptide Mimetics from a Phage Display Library

Peptide mimics were isolated from a phage display library using a library purchased from New England Biolabs called the PhD-12 Phage Display Peptide Library Kit (Cat No. #E8110S). The PhD-12 Phage Display Peptide Library Kit is based on a combinatorial library of random peptide 12-mers fused to a minor coat protein (pIII) of M13 phage. The displayed peptide 12-mers are expressed at the N-terminus of pIII coat protein. The library consists of ~2.7×10$^9$ electroporated sequences, amplified once to yield ~55 copies of each sequence in 10 µl of the supplied phage. The library is usually panned 3-4 times on the subject of study (usually antibody, but can use receptors, ligands etc.) with increasing stringency of washing at each step followed by analysis of individual clones for a consensus sequence binding to the test subject.

EXAMPLE 2

Analysis of Peptide Mimetics from a Phage Display Library

Figure 2:
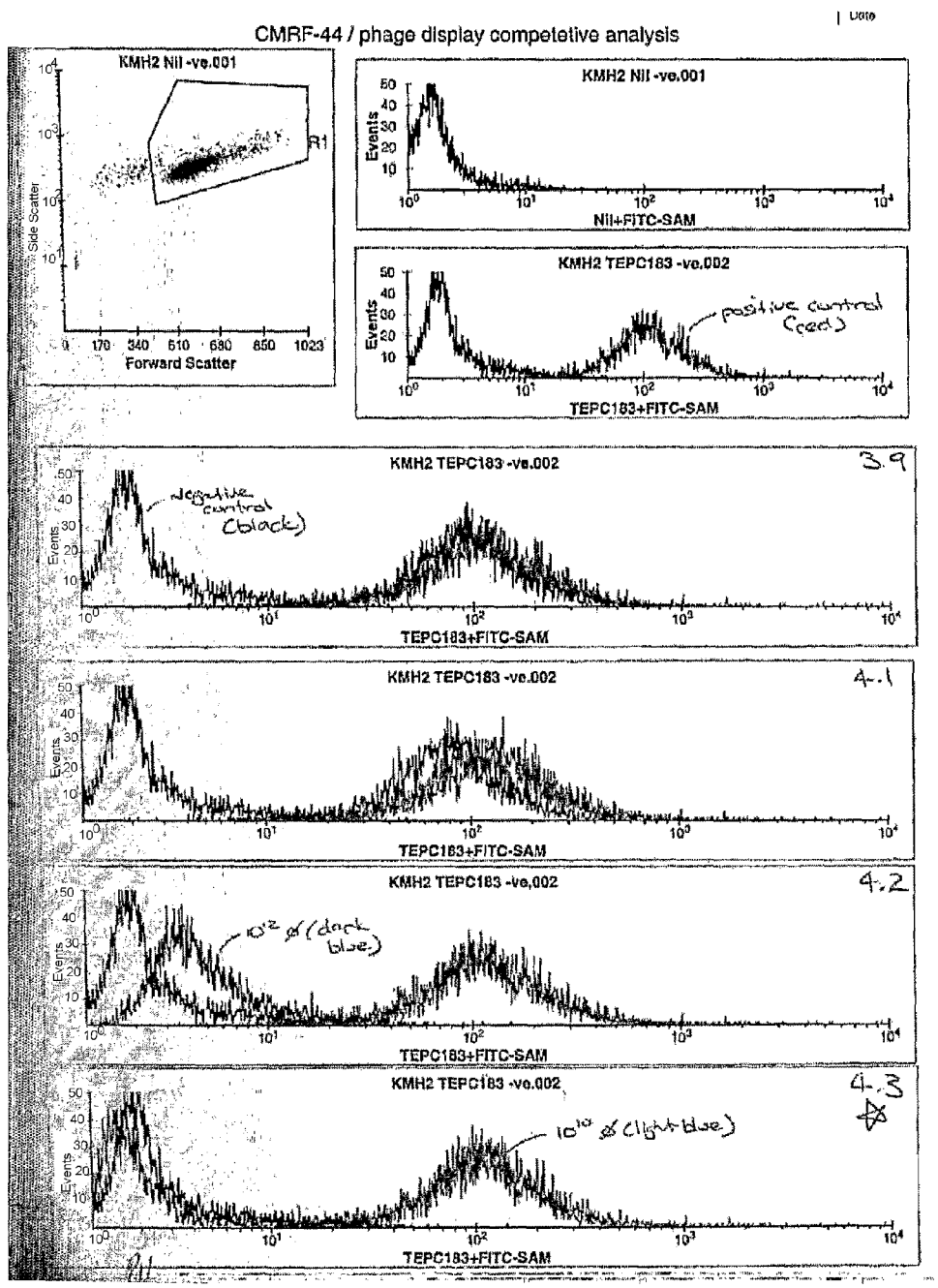
FIG. 2 is a graphical representation of competitive binding of peptide clones with natural antigen on cell surface.

The consensus sequence of any peptides isolated from the library were be determined according to methods known to a person skilled in the art. ELISAs were then used to determine the binding of individual peptide phage clones or synthetic peptides (with or without repeats of the consensus sequence) to the original target (FIG. 1). Competitive binding assays were also used and analysed by FACS to determine true binding of the peptide sequences to the binding site of the target compared with the "natural" ligand or epitope (FIG. 2). Sequence analysis of the consensus sequence can determine what type of ligand is binding to the target or could give a true epitope, which may be used for database searches to find possible full-length sequences.

Figure 4:
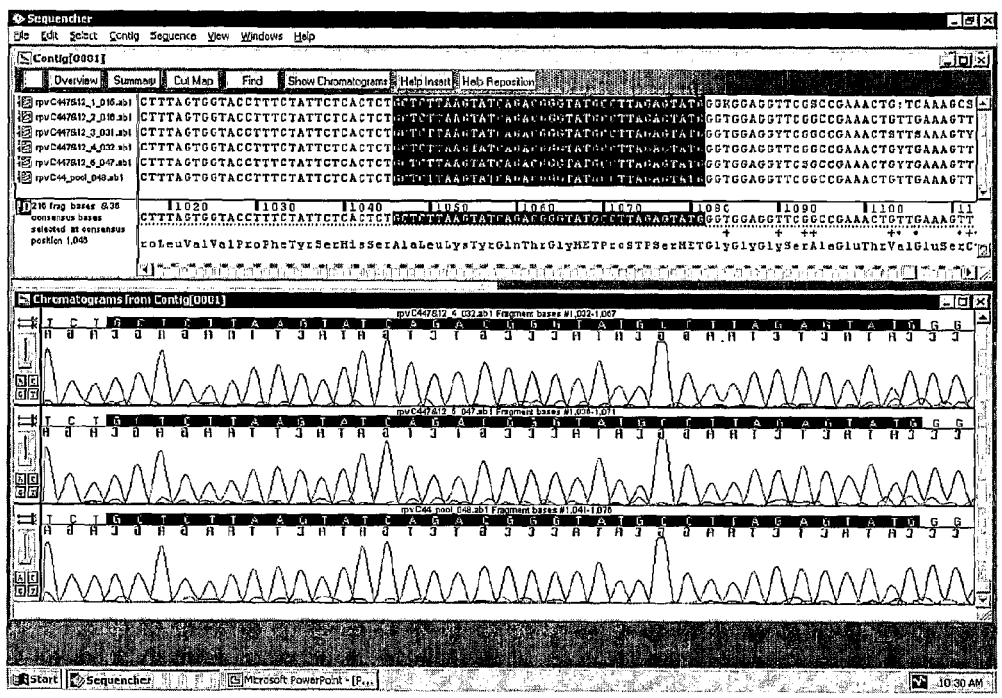
FIG. 4 is a graphical representation of sequence results of $3^{rd}$ round combined 7 and 12-mer phage peptide library panning (CMRF44Ab).

A consensus peptide sequence was identified for peptides which bind to CMRF44Ab from the 12-mer libraries using ELISA. Subsequent FACS analysis of phage peptide blocking of binding of CMRF44Ab to the cell surface also confirmed the peptide sequence. The peptide sequence appeared to be constrained to the N-terminus and the best sequence was AQKYQ (SEQ ID NO: 2) with apparent strong conservation at 1st, 3rd and 5th residues. A family of sequences were also identified and included ALKYQ (SEQ ID NO: 4), ALKEQ (SEQ ID NO: 5) and APKQQ (SEQ ID NO: 3). Further repeat panning of PhD-7 library was carried out to confirm the peptide sequence and identify other possible CMRF44 peptide antigen mimic sequences. Sequencing of 4th round clones did not identify any further similar peptides to those previously found with the 12-mer libraries. Also, 3 rounds of repeat panning was carried out on combined 7-mer and 12-mer libraries (pooled together) with acid elution. Several clones sequences as well as pool of 3 round eluate. Results for CMRF-44 show an enrichment of the clone: ALKYQTGMPQSM (SEQ ID NO: 6) in both individual clones and the main strongest sequence in the pooled 3rd round eluate (FIG. 4).

Figure 3:
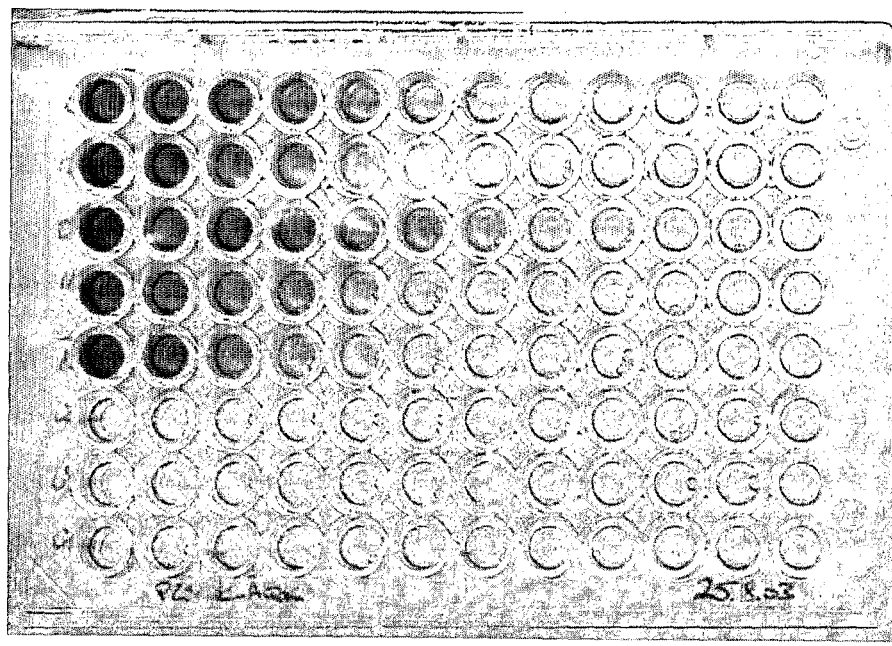
FIG. 3 is a photographic representation of an ELISA result of mice immunized with an immunizing version of the peptide, AQKYQGIHIWPR (SEQ ID NO:10).

An immunizing peptides comprising the amino acid sequence of SEQ ID NO:10 optionally linked to T and/or B cell epitope capable of binding to the CMRF44Ab are used to immunize mice in order to generate other antibodies of the same specificity as CMRF44Ab. A particularly useful embodiment a measles T-helper polypeptide is linked to the end terminal portion of SEQ ID NO:10. Upon processing, the T-helper measles portion is removed. FIG. 3 is an example of the latter peptide used to immunize different mice. Each row represents a different mouse in serial dilutions of serum.

EXAMPLE 3

BIACORE Analysis of CMRF44Ab Binding to Peptide Mimetics

Chip 179 Channel 1

Figure 5:
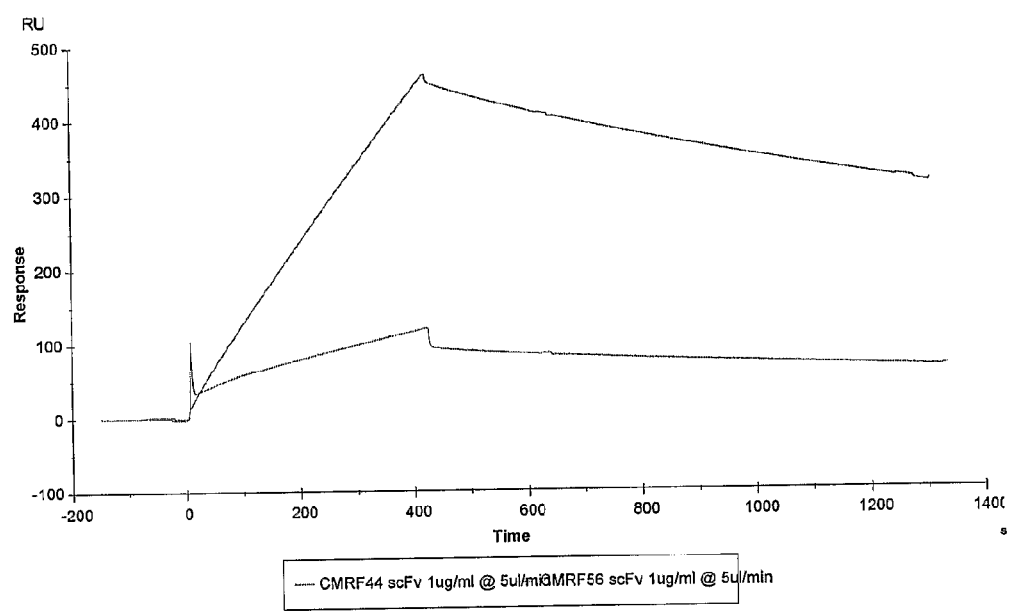
FIG. 5 is a graphical representation of CMRF44 scFv binding to immobilized peptide mimetic at 5 µl/min.
Figure 6:
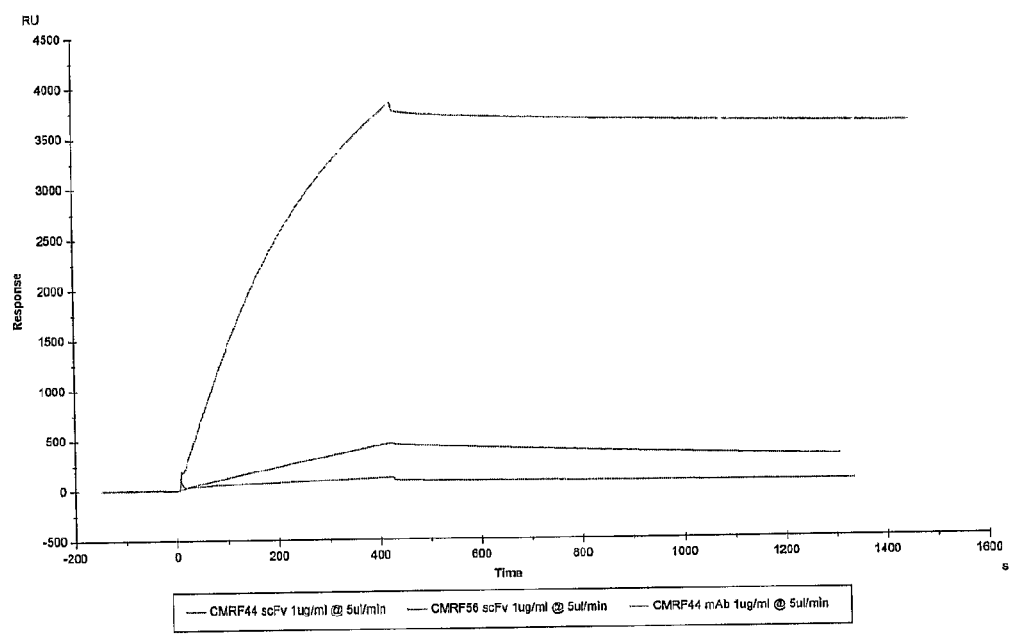
FIG. 6 is a graphical representation of CMRF44 scFv and CMRF44Ab binding to immobilized peptide mimetic at 5 µl/min
Figure 7:
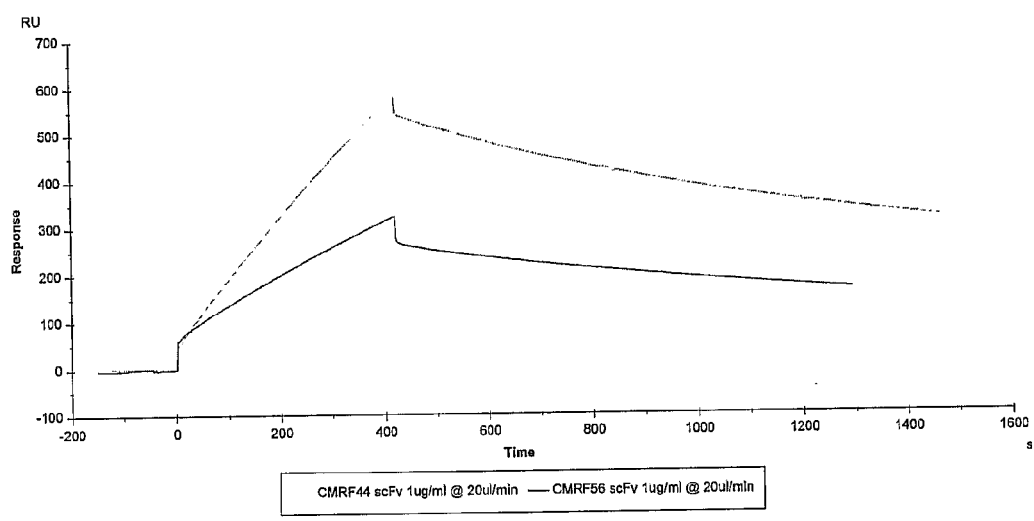
FIG. 7 is a graphical representation of CMRF44 scFv binding to immobilized peptide mimetic at 20 µl/min.
Figure 8:
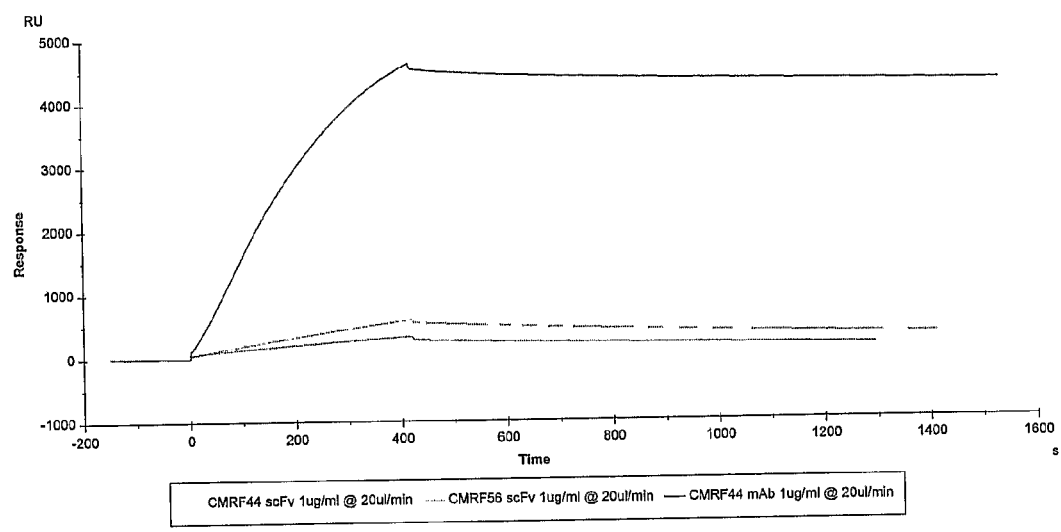
FIG. 8 is a graphical representation of CMRF44 scFv and CMRF44Ab binding to immobilized peptide mimetic at 20 µl/min
Figure 9:
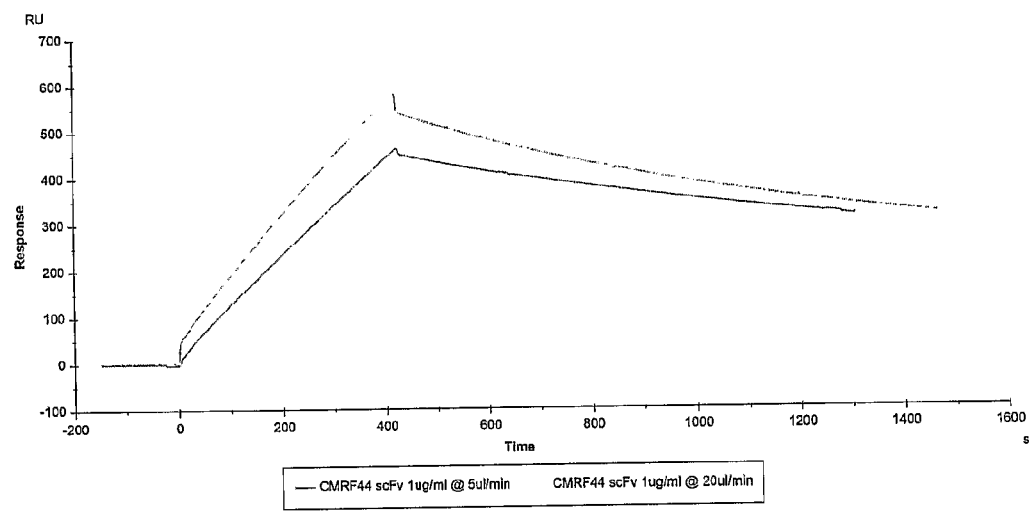
FIG. 9 is a graphical representation of CMRF44 scFv binding to immobilized peptide mimetic at 5 and 20 µl/min.
Figure 10:
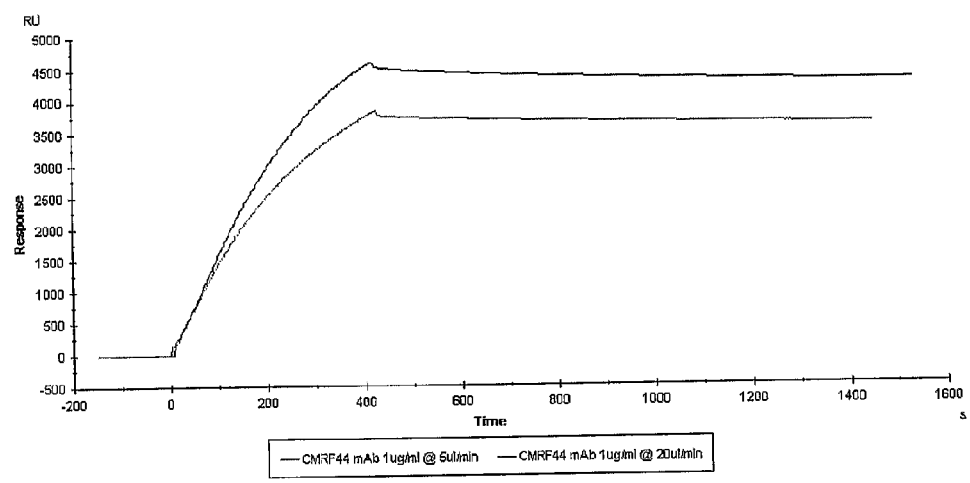
FIG. 10 is a graphical representation of CMRF44Ab binding to immobilized peptide mimetic at 5 and 20 µl/min.

The streptavidin chip was initially conditioned with 5 μl of 1M NaCl in 50 mM NaOH at 5 μl/min. Initial RU on surface was 16166.1RU. Approximately 570RU was removed to have final RU on surface before immobilisation of 15597RU. The chip then had 447RU of CMRF peptide mimic immobilised. 2×10 μl of peptide CMRF44 mimic-LC biotin diluted 1/500 to 10 μg/ml was then injected. This was then washed 3× with 5 μl injections of 1M NaCl in 50 mM NaOH to give the final RU immobilised as 447RU. CMRF44 scFv was then injected across channel 1 at 1 μg/ml at a flow rate of 5 μl/min, injecting 35 μl and regenerating with 10 μl of 1M NaCl in 50 mM NaOH (FIG. 5). CMRF44Ab at 1 μg/ml was also tested at a flow rate of 5 μl/min, injecting 35 μl and regenerating with 10 μl of 1M NaCl in 50 mM NaOH (FIG. 6). The flow rate was then increased to 20 μl/min, injecting 140 μl at 1 μg/ml and regenerating with 20 μl of 1M NaCl in 50 mM NaOH (FIGS. 7 and 8). The results of 5 and 20 μl/min flow rates were then compared (FIGS. 9 and 10).

Chip 179 Channel 2 (Streptavidin Blank Control)

Figure 11:
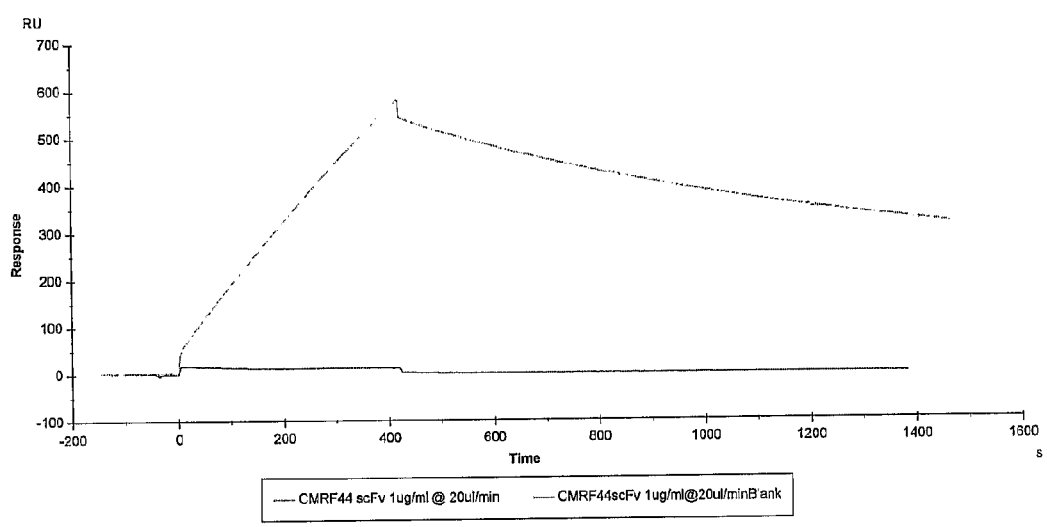
FIG. 11 is a graphical representation of CMRF44 scFv binding to immobilized peptide mimetic (channel 1) at 20 µl/min compared to blank strepavidin surface (channel 2).
Figure 12:
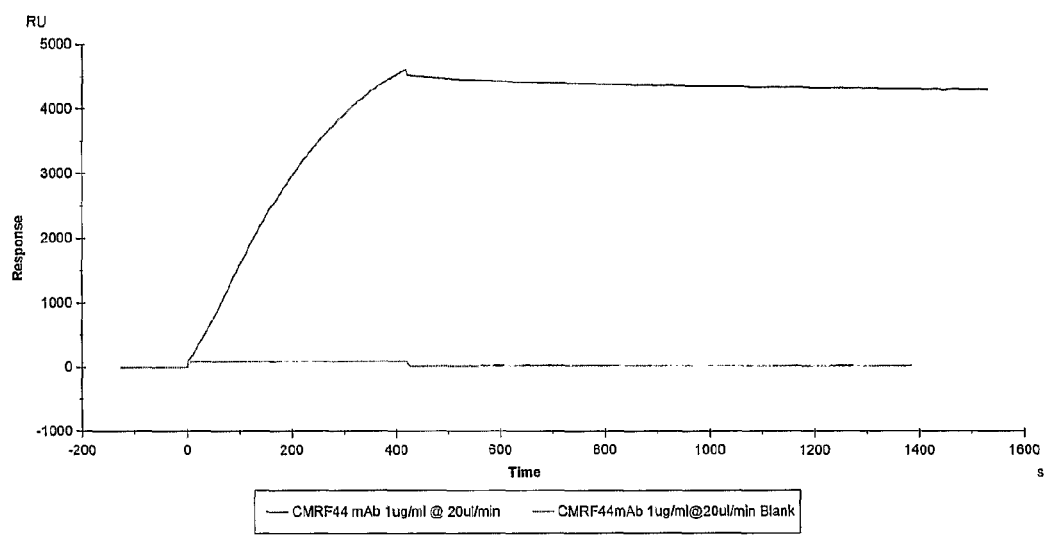
FIG. 12 is a graphical representation of CMRF44Ab binding to immobilized peptide mimetic (channel 1) at 20 µl/min compared to blank strepavidin surface (channel 2).

The chip was initially conditioned with 5 μl of 1M NaCl in 50 mM NaOH at 5 μl/min. Initial RU on surface was 15171RU. Approximately 186RU was removed to have final RU on surface before immobilisation of 15384RU. CMRF44 scFv was injected across channel 1 and Channel 2 (Strep Blank) at 1 μg/ml at a flow-rate of 20 μl/min, injecting 140 μl and regenerating with 20 μl of 1M NaCl in 50 mM NaOH (FIG. 11). CMRF44Ab at 1 μg/ml was also tested at a flow rate of to 20 μg/min, injecting 140 μl and regenerating with 20 μl of 1M NaCl in 50 mM NaOH (FIG. 12).

Figure 13:
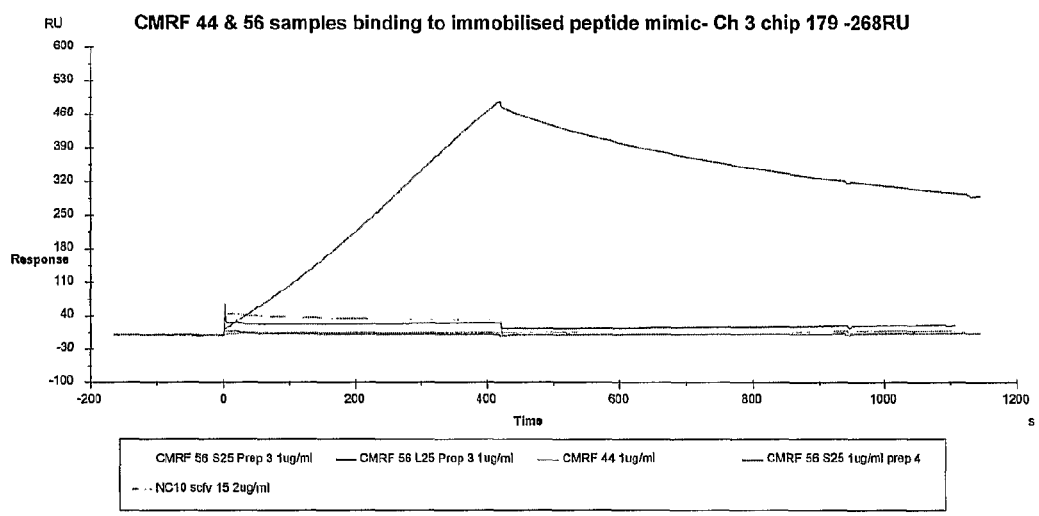
FIG. 13 is a graphical representation of CMRF44 scFv binding to immobilized peptide mimetic at high density.
Figure 14:
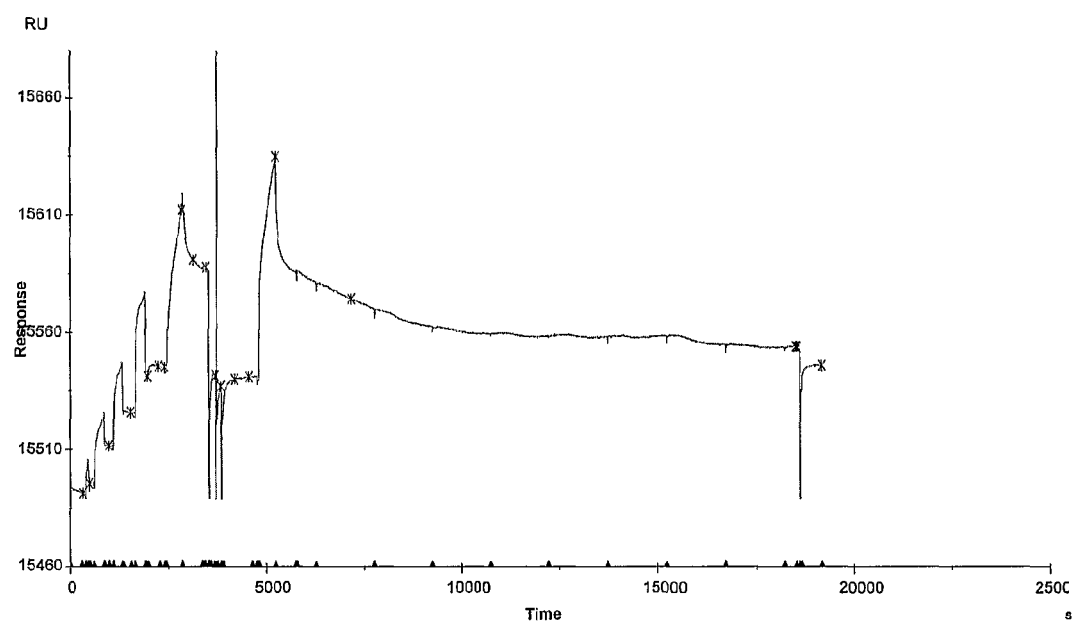
FIG. 14 is a graphical representation of CMRF44 scFv binding to immobilized peptide mimetic at low density.
Figure 15:
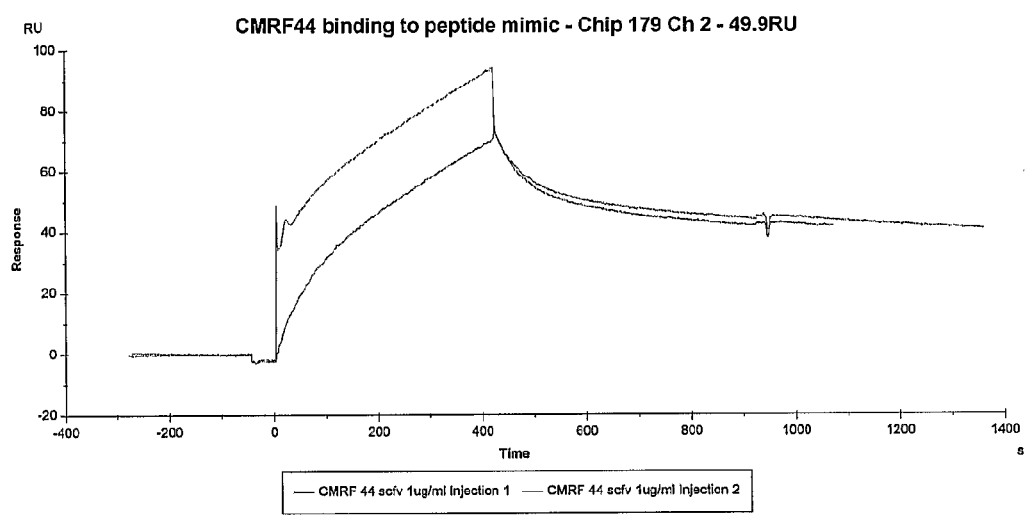
FIG. 15 is a graphical representation of CMRF44 scFv binding to immobilized peptide mimetic at low and high density.

The CMRF44 scFv at 1 μg/ml was also analysed over a peptide mimetic surface at high density (FIG. 13) and low density (FIG. 14) and using channel 1 as high surface (447RU) and channel 2 as low surface (49.9RU) (FIG. 15).

Figure 16:
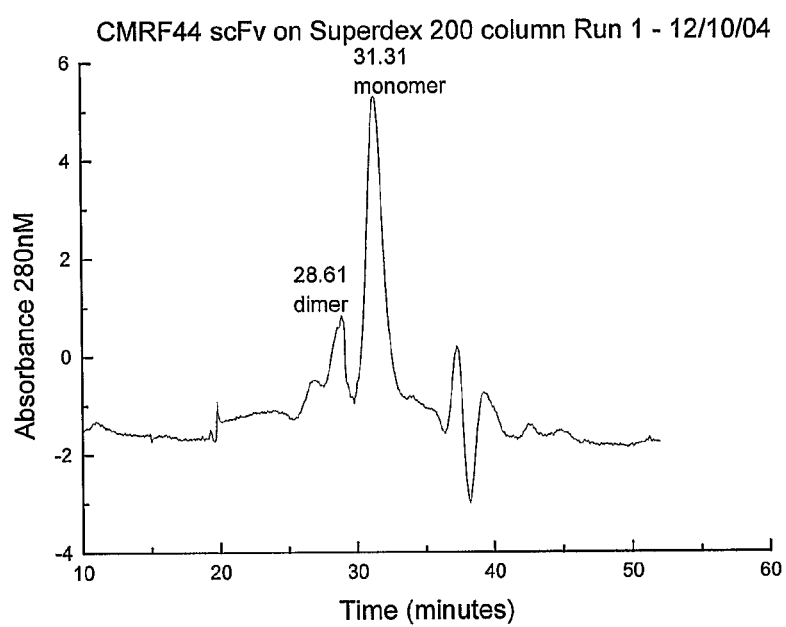
FIG. 16 is a graphical representation showing CMRF44 scFv monomers and dimers.
Figure 17:
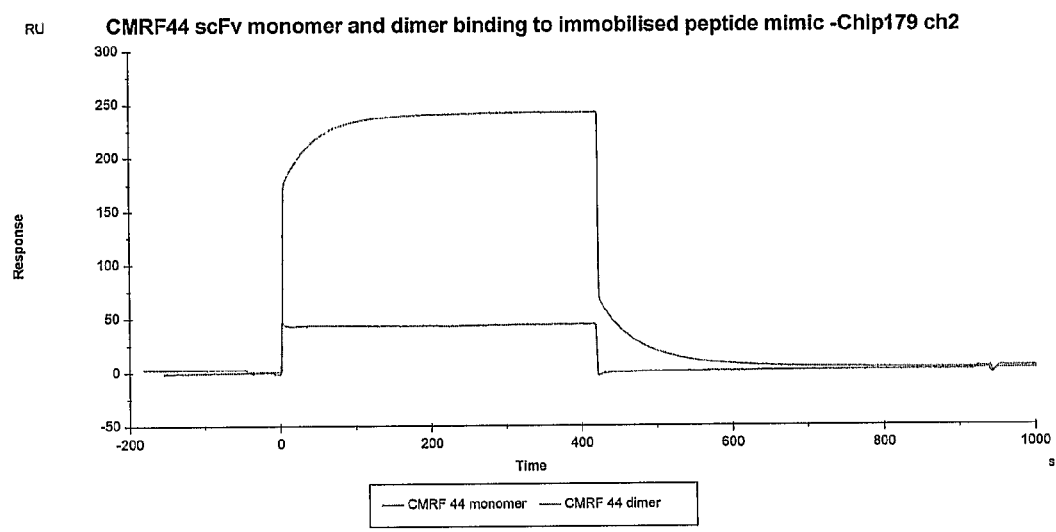
FIG. 17 is a graphical representation showing CMRF44 scFv monomers and dimers binding to immobilized peptide mimetic at low density.
Figure 18:
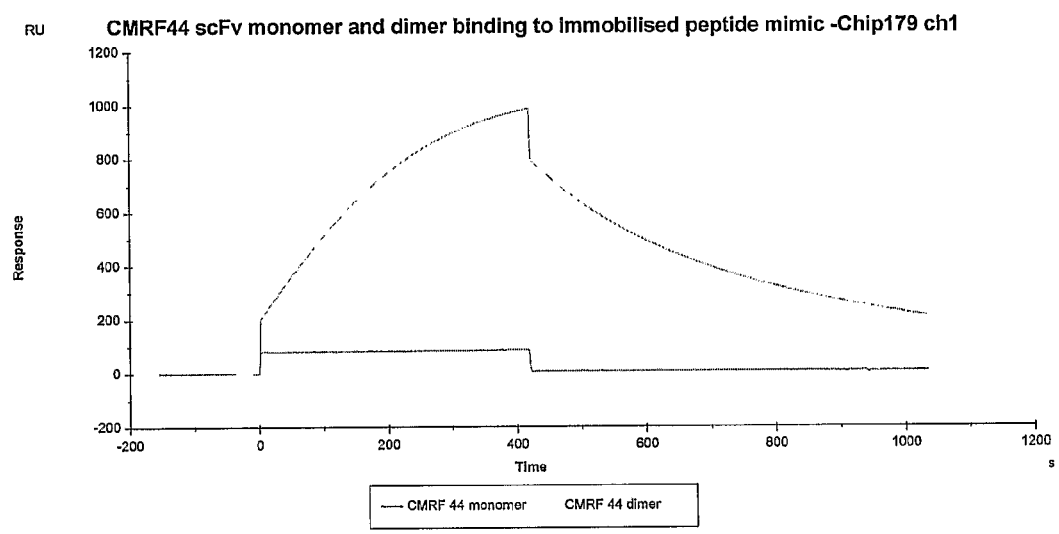
FIG. 18 is a graphical representation showing CMRF44 scFv monomers and dimers binding to immobilized peptide mimetic at high density.
Figure 19:
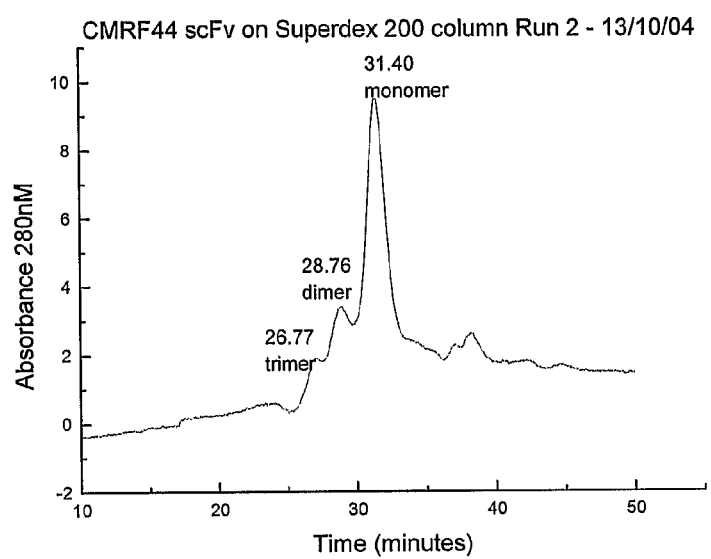
FIG. 19 is a graphical representation showing CMRF44 scFv monomers, dimers and trimers.
Figure 20:
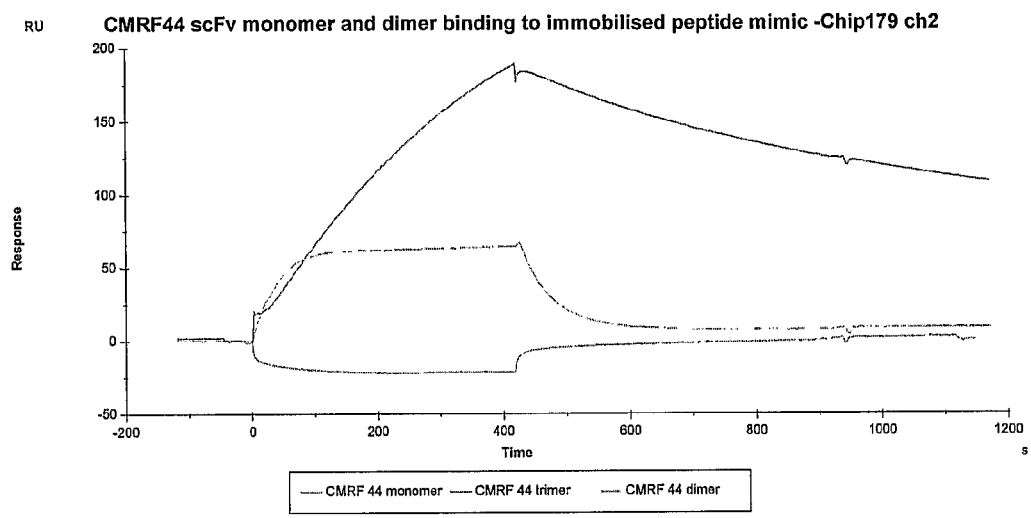
FIG. 20 is a graphical representation showing CMRF44 scFv monomers, dimers and trimers binding to immobilized peptide mimetic at low density.
Figure 21:
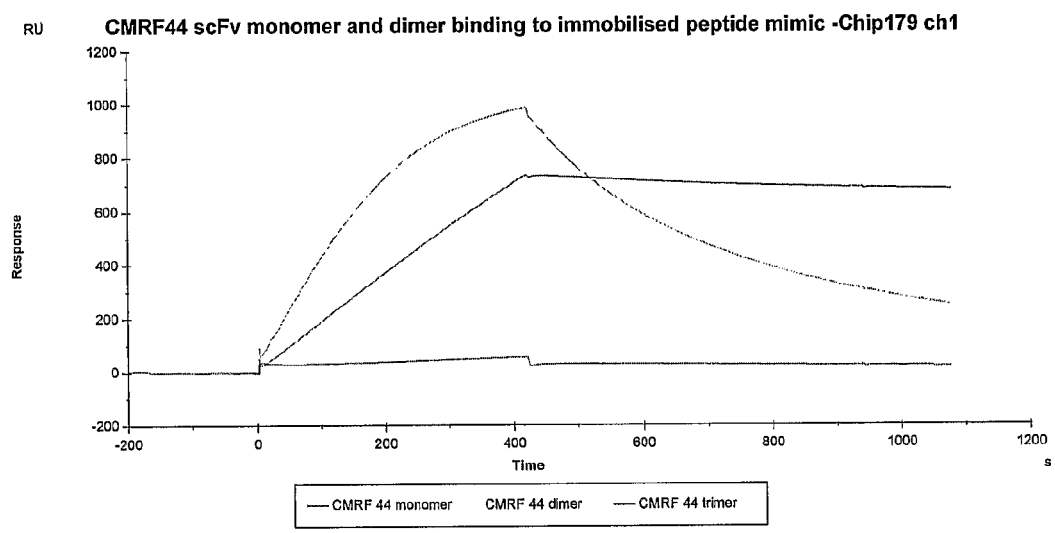
FIG. 21 is a graphical representation showing CMRF44 scFv monomers, dimers and trimers binding to immobilized peptide mimetic at high density.

CMRF44 scFv monomers and dimers (FIG. 16) were also run over a low density peptide mimetic surface (FIG. 17) and high density peptide mimetic surface (FIG. 18). CMRF44 scFv trimers (FIG. 19) were also run over a low density peptide mimetic surface (FIG. 20) and high density peptide mimetic surface (FIG. 21).

EXAMPLE 4

Peptide Specificity

Figure 22:
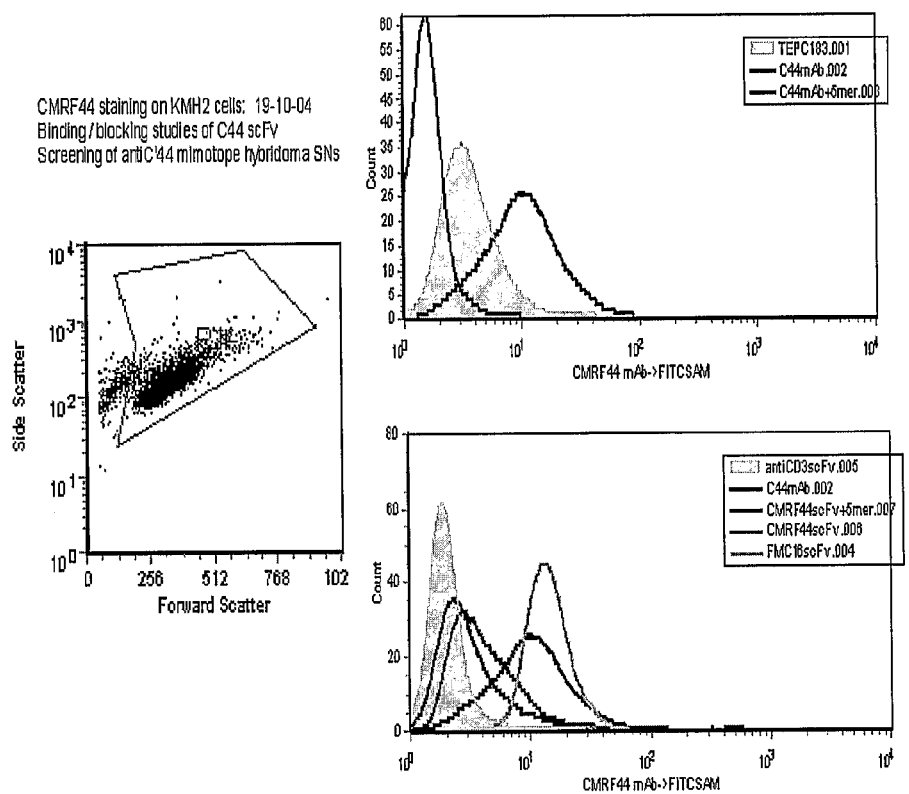
FIG. 22 is a graphical representation of FACS data showing binding of CMRF44Ab and scFv binding to KM-H2 cells and blocking of binding to natural antigen by competition with peptide mimic.

FACS analysis demonstrates blocking of the CMRF44Ab with the 5-mer peptide AQKYQ alone, as well as blocking of the engineered CMRF44 scFv (FIG. 22).

EXAMPLE 5

New Antibodies Specific for CMRF44Ag

Figure 23:
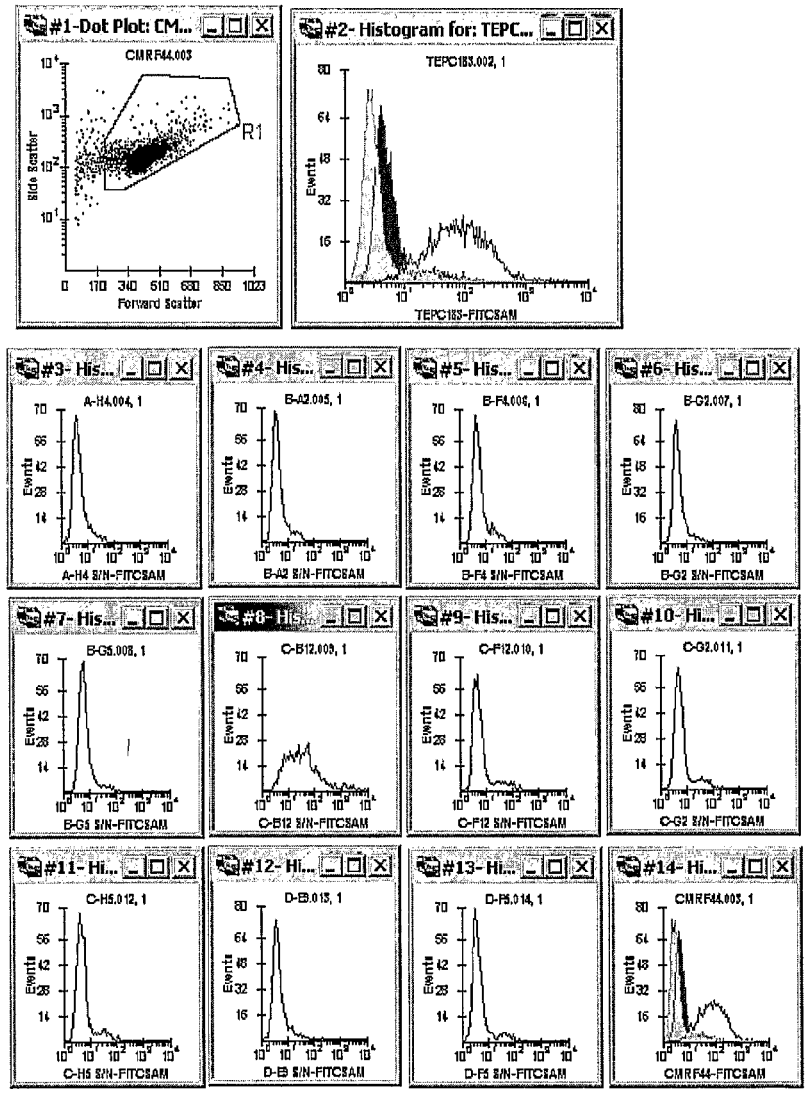
FIG. 23 is a graphical representation showing the development of a new antibody which is specific for CMRF44Ag.

A new antibody specific for CMRFAg was developed by immunizing mice with a peptide mimetic that was identified by ELISA and confirmed by staining of the CMRF44 cell line KM-H2 (FIG. 23).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Bibliography

Adams et al, *Cancer Res* 53:4026-4034, 1993
Altschul et al, *Nucl Acids Res* 25:3389-3402, 1997
Bandyopadhyay and Temin, *Mol Cell Biol* 4:749-754, 1984
Berkner, *Curr Top Microbiol Immunol* 158:39-66, 1992
Berglund et al, *Biotechnology* 11:916-920, 199
Berkner et al, *BioTechniques* 6:616-629, 1988
Blazar et al, *Blood* 85:2607-2618, 1995
Bonner and Laskey, *Eur J Biochem* 46:83-88, 1974
Breakefield and Geller, *Mol Neurobiol* 1:339-371, 1987

Buchschacher and Panganiban, *J Virol* 66:2731-2739, 1982
Calm et al, *Transplantation* 60:939-942, 1995
Chothia et al, *J Mol Biol* 196:901-917, 1987
Chothia et al, *J Mol Biol* 227:799-817
Cumber et al, *J Immunol* 149:120-126, 1992
Davies and Riechmann, *FEBS Lett* 339:285-290, 1994
Deeg et al, *Blood* 98:2052-2058, 2001
Egleton and Davis, *Peptides* 18:1431-1439, 1997
Erickson et al, *Science* 249:527-533, 1990
Fearnley et al, *Blood* 89:3708-3716, 1997
Fink et al, *Hum Gene Ther* 3:1-19, 1992
Fink et al, *Ann Rev Neurosci* 19:265-287, 1996
Freese et al, *Biochem Pharmaco.* 40:2189-2199, 1990
Gefter et al, *Somatic Cell Genet* 3:231-236, 1977
Glockshuber et al, *Biochem* 29:1363-1367, 1990
Gorziglia and Kapikian, *J Virol* 66:4407-4412, 1992
Gribben et al, *Blood* 87:4887-4893, 1996
Grouard et al, *J Exp Med* 185:1101-1111, 1997
Hamers-Casterman et al, *Nature* 363:446-448, 1993
Hart, *Blood* 90:3245-3287, 1997
Helseth et al, *J Virol* 64:2416-2420, 1990
Hock et al, *Immunology* 83:573-581, 1994
Hodgson, *Bio/Technology* 9:19-21, 1991
Johnson et al, *J Virol* 66:2952-2965, 1992
Jones et al, *Nature* 321:522-525, 1986
Kirk et al, *Proc Natl Acad Sci USA* 94:8789-8794, 1997
Kirk et al, *Nat Med* 5:686-693, 1999
Koenen and Joosten, *Blood* 95:3153-3161, 2000
Köhler and Milstein, *Nature* 256:495-499, 1975
Köhler and Milstein, *Eur J Immunol* 6:511-519, 1976
Kostelny et al, *J Immunol* 148:1547-1553, 1992
Kozbor et al, *Methods in Enzymology* 121:140-167, 1986
Krebber et al, *J Immunol Methods* 201:35-55, 1997
Ku and Schutz, *Proc Natl Acad Sci USA* 92:6552-6556, 1995
Langer, *Science* 249:1527-1533, 1990
Liu et al, *Proc Natl Acad Sci USA* 84:3439-3443, 1987
Madzak et al, *J Gen Virol* 73:1533-1536, 1992
Mann and Baltimore, *J Virol* 54:401-407, 1985
Margolskee, *Curr Top Microbiol Immunol* 158:67-95, 1992
Marmur and Doty, *J Mol Biol* 5:109-118, 1962
Miller, *Curr Top Microbiol Immunol* 158:1-24, 1992
Miller et al, *Mol Cell Biol* 5:431-437, 1985
Miller et al, *J Virol* 62:4337-4345, 1988
Moss, *Curr Top Microbiol Immunol* 158: 5-38, 1992
Moss, *Proc Natl Acad Sci USA* 93:11341-11348, 1996
Muzyczka, *Curr Top Microbiol Immunol* 158:97-129, 1992
Naldini et al, *Science* 272:263-267, 1996
Ohi et al, *Gene* 89:279-282, 1990
Page et al, *J Virol* 64:5270-5276, 1990
Petropoulos et al, *J Virol* 66:3391-3397, 1992
Plünckthun, *Biochem* 31:1579-1584, 1992
Quantin et al, *Proc Natl Acad Sci USA* 89:2581-2584, 1992
Reiter et al, *J Biol Chem* 269:18327-18331, 1994
Reiter et al, *Biochem* 33:5451-5459, 1994
Reiter et al, *Cancer Res* 54:2714-2718, 1994
Riechmann et al, *Nature* 332:323-327, 1988
Robinson et al, *Eur J Immunol* 29:2769-2778, 1999
Rosenfeld et al, *Cell* 68:143-155, 1992
Russell and Hirata, *Nat Genetics* 18:323-328, 1998
Schneider et al, *Nat Genetics* 18:180-183, 1998
Shimada et al, *J Clin Invest* 88:1043-1047, 1991
Shulman et al, *Nature* 276:269-270, 1978
Sorge et al, *Mol Cell Biol* 4:1730-1737, 1984
Stratford-Perricaudet et al, *Hum Gene Ther* 1:241-256, 1990
Trowbridge, *J Exp Med* 148:313-323, 1978
Verhoeyen et al, *Science* 239:1534-1536, 1988
Volk et al, *J Virol* 42:220-227, 1982
Ward et al, *Nature* 341:544-546, 1989
Webber et al, *Mol Immunol* 32:249-258, 199
Wells, *Methods Enzymol* 202:2699-2705, 1991
Wilkinson et al, *Nucleic Acids Res* 20:233-2239, 1992
Winter and Milstein, *Nature* 349:293-299, 1991

---

What is claimed is:

1. An isolated peptide comprising the amino acid sequence set forth in SEQ NO: 10 (AQKYQGIHIWPR), wherein said peptide binds to CMRF44Ab.

2. The isolated peptide of claim 1 consisting of the amino acid sequence set forth in SEQ ID NO: 10.

3. The peptide of claim 1 for use in generating antibody which specifically binds CMRF44 antigen.

4. The peptide of claim 1 for use in screening for antibodies which specifically bind CMRF44 antigen.

5. The peptide of claim 1 for use in assessing binding specificity of a CMRF44-like antibody.

6. The peptide of claim 1 for use as a release agent in a method for selection of CMRF44 expressing cells.

* * * * *

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid

<400> SEQUENCE: 1

Ala Xaa Lys Xaa Gln
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2
```

```
Ala Gln Lys Tyr Gln
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Ala Pro Lys Gln Gln
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Ala Leu Lys Tyr Gln
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Ala Leu Lys Glu Gln
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide

<400> SEQUENCE: 6

Ala Leu Lys Tyr Gln Thr Gly Met Pro Gln Ser Met
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide

<400> SEQUENCE: 7

Ala Leu Lys Glu Gln Gly Trp Pro Gly Gln Pro Leu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide

<400> SEQUENCE: 8

Ala Leu Lys Tyr Gln Thr Gly Met Pro Gln Ser Met
```

```
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide

<400> SEQUENCE: 9

Ala Pro Lys Gln Gln Tyr Pro Trp Trp Tyr Ser Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

Ala Gln Lys Tyr Gln Gly Ile His Ile Trp Pro Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Tyr His Thr Leu Gln Ala Pro Thr Pro Pro Gly Trp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide

<400> SEQUENCE: 12

Val Pro Tyr Ile Tyr Val Asn Glu Pro Leu Ser Arg
1               5                   10
```